(12) United States Patent
Krishnan

(10) Patent No.: US 9,220,725 B2
(45) Date of Patent: Dec. 29, 2015

(54) CATIONIC LATEX AS A CARRIER FOR BIOACTIVE INGREDIENTS AND METHODS FOR MAKING AND USING THE SAME

(75) Inventor: Venkataram Krishnan, Cary, NC (US)

(73) Assignee: Mallard Creek Polymers, Inc., Charlotte, NC (US)

( * ) Notice: Subject to any disclaimer, the term of this patent is extended or adjusted under 35 U.S.C. 154(b) by 932 days.

(21) Appl. No.: 11/895,541

(22) Filed: Aug. 24, 2007

(65) Prior Publication Data

US 2008/0057049 A1 Mar. 6, 2008

Related U.S. Application Data

(60) Provisional application No. 60/839,973, filed on Aug. 24, 2006.

(51) Int. Cl.
| | |
|---|---|
| *A01N 25/10* | (2006.01) |
| *A01N 37/44* | (2006.01) |
| *A61K 31/7048* | (2006.01) |
| *A61K 31/722* | (2006.01) |
| *C08F 6/00* | (2006.01) |
| *C08F 220/34* | (2006.01) |
| *C08F 220/28* | (2006.01) |

(52) U.S. Cl.
CPC .............. *A61K 31/722* (2013.01); *A01N 25/10* (2013.01); *A01N 37/44* (2013.01); *A61K 31/7048* (2013.01); *C08F 6/003* (2013.01); *C08F 220/34* (2013.01); *C08F 2220/286* (2013.01)

(58) Field of Classification Search
CPC ....... A01N 37/44; A01N 31/08; A01N 31/14; A01N 41/10; A01N 43/40; A01N 43/653; A01N 59/16; A01N 25/10; A01N 2300/00; A61K 31/7048; A61K 31/722; C08F 220/34; C08F 2220/286; C08F 6/003
See application file for complete search history.

(56) References Cited

U.S. PATENT DOCUMENTS

| 2,882,157 A | 4/1959 | Thompson et al. |
|---|---|---|
| 2,972,535 A | 2/1961 | Laasko et al. |
| 3,140,227 A | 7/1964 | Roth et al. |
| 3,262,807 A | 7/1966 | Sterman et al. |
| 3,296,196 A | 1/1967 | Lamoreaux |
| 3,450,794 A | 6/1969 | Ebneth et al. |
| 3,592,805 A | 7/1971 | Szabo et al. |

(Continued)

FOREIGN PATENT DOCUMENTS

| DE | 2447611 | 4/1975 |
|---|---|---|
| DE | 19833062 A1 | 2/2000 |

(Continued)

OTHER PUBLICATIONS

Napper, "Steric Stabilization", *J. Colloid Interface Sci.*, 58:2, 390-407 (1977), Abstract: 86: 107053, XP002125110.
Ottewill et al., "Preparation of Core-Shell Polymer Colloid Particles by Encapsulation", *Colloid & Polymer Science*, pp. 274-283 (1997).
International Search Report, PCT/US99/17670, International Filing Date: Aug. 6, 1999.
"Polymer Compositions for Cationic Electrodepositable Coatings", *Journal of Coatings Technology*, vol. 54; No. 686, Mar. 1982, Kordomenos, P.I., et al., pp. 33-41.
Michelsen, T., "Building Materials (Survey)," *Kirk-Othmer Encyclopedia of Chemical Technology*, (1992 4th ed.), vol. 4, pp. 618-619.
"Polymer Compositions for Cationic Electrodepositable Coatings," *Journal of Coatings Technology*, vol. 54, No. 686, Mar. 1982, Kordomenos, P.I., et al., pp. 33-41.
Rompp Chemie Lexikon (Chemical Dictionary), vol. 5, PI-S (1995), pp. 3558-3559.
Supplemental European Search Report for European Patent Application No. 07811542 dated Dec. 13, 2010.
English translation of Office Action mailed on Nov. 20, 2012 for Japanese Application No. 2009-525656.
English translation of Chinese Office Action mailed on Mar. 26, 2012 for Chinese Application No. 200780034318.X.
English translation of Office Action mailed on Jul. 11, 2012 for Russian Application No. 2010149893.

*Primary Examiner* — Aradhana Sasan
(74) *Attorney, Agent, or Firm* — Womble Carlyle Sandridge & Rice, LLP

(57) ABSTRACT

This invention relates to latex compositions that incorporate at least one bioactive component such as an antibacterial or antifungal agent, and methods for making and using such latex compositions. The latex compositions disclosed herein can be prepared by the emulsion polymerization of the latex component monomers in the presence of the at least one bioactive component.

27 Claims, 4 Drawing Sheets

(56) References Cited

U.S. PATENT DOCUMENTS

| | | |
|---|---|---|
| 3,619,200 A | 11/1971 | Ferguson et al. |
| 3,753,716 A | 8/1973 | Ishihara et al. |
| 3,872,128 A | 3/1975 | Byck |
| 4,026,941 A | 5/1977 | Login et al. |
| 4,029,694 A | 6/1977 | Weipert et al. |
| 4,070,189 A | 1/1978 | Kelley et al. |
| 4,080,315 A | 3/1978 | Login |
| 4,081,419 A | 3/1978 | Shimizu et al. |
| 4,093,676 A | 6/1978 | Weipert et al. |
| 4,098,842 A | 7/1978 | Login |
| 4,104,443 A | 8/1978 | Latta et al. |
| 4,147,550 A | 4/1979 | Campbell et al. |
| 4,226,747 A | 10/1980 | Roncari |
| 4,229,554 A | 10/1980 | Newkirk et al. |
| 4,234,381 A | 11/1980 | Killam |
| 4,256,800 A | 3/1981 | Stockhausen et al. |
| 4,332,919 A | 6/1982 | Kobayashi et al. |
| 4,361,623 A | 11/1982 | Newkirk et al. |
| 4,366,238 A | 12/1982 | Yokoyama et al. |
| 4,377,667 A | 3/1983 | Sakurai et al. |
| 4,384,078 A | 5/1983 | Ohya et al. |
| 4,416,668 A | 11/1983 | Thompson |
| 4,500,517 A | 2/1985 | Luss |
| 4,506,070 A | 3/1985 | Ben |
| 4,543,390 A | 9/1985 | Tanaka et al. |
| 4,546,140 A | 10/1985 | Shih |
| 4,632,881 A | 12/1986 | Trotz et al. |
| 4,668,748 A | 5/1987 | Hardam et al. |
| 4,722,965 A | 2/1988 | Wong et al. |
| 4,810,567 A | 3/1989 | Calcaterra et al. |
| 4,831,098 A | 5/1989 | Watanabe et al. |
| 4,841,021 A | 6/1989 | Katritzky et al. |
| 4,855,127 A | 8/1989 | Abrutyn et al. |
| 4,857,590 A | 8/1989 | Gaggar et al. |
| 4,859,727 A | 8/1989 | Sasaki et al. |
| 4,877,687 A | 10/1989 | Azegami et al. |
| 4,891,306 A | 1/1990 | Yokoyama et al. |
| 4,898,908 A | 2/1990 | Lahalih et al. |
| 4,900,543 A | 2/1990 | Ritter et al. |
| 4,900,544 A | 2/1990 | Ritter et al. |
| 4,920,166 A | 4/1990 | Buysch et al. |
| 4,931,506 A | 6/1990 | Yu |
| 4,948,720 A | 8/1990 | Chen et al. |
| 4,954,636 A | 9/1990 | Merianos et al. |
| 4,997,697 A | 3/1991 | Malhotra |
| 4,999,249 A | 3/1991 | Deschler et al. |
| 5,010,139 A | 4/1991 | Yu |
| 5,024,840 A | 6/1991 | Blakely et al. |
| 5,043,195 A | 8/1991 | Skrivseth |
| 5,059,629 A | 10/1991 | Patton et al. |
| 5,061,752 A | 10/1991 | Buysch et al. |
| 5,142,010 A | 8/1992 | Olstein |
| 5,153,321 A | 10/1992 | Finter et al. |
| 5,175,059 A | 12/1992 | Yamamoto et al. |
| 5,290,894 A | 3/1994 | Melrose et al. |
| 5,314,924 A | 5/1994 | Lee |
| 5,346,956 A | 9/1994 | Gnanou |
| 5,358,688 A | 10/1994 | Robertson |
| 5,369,179 A | 11/1994 | Havens |
| 5,370,981 A | 12/1994 | Krafft et al. |
| 5,372,804 A | 12/1994 | Khoshdel et al. |
| 5,403,640 A | 4/1995 | Krishnan et al. |
| 5,494,987 A | 2/1996 | Imazato et al. |
| 5,512,055 A * | 4/1996 | Domb et al. .................. 604/265 |
| 5,515,117 A | 5/1996 | Dziabo et al. |
| 5,518,788 A | 5/1996 | Invie |
| 5,520,910 A | 5/1996 | Hashimoto et al. |
| 5,536,494 A | 7/1996 | Park |
| 5,536,861 A | 7/1996 | Robertson |
| 5,591,799 A | 1/1997 | Bott et al. |
| 5,645,968 A | 7/1997 | Sacripante |
| 5,654,369 A | 8/1997 | Tsubaki et al. |
| 5,700,742 A | 12/1997 | Payne |
| 5,773,507 A | 6/1998 | Incorvia et al. |
| 5,798,048 A | 8/1998 | Ries |
| 5,830,934 A | 11/1998 | Krishnan |
| 5,830,983 A | 11/1998 | Alex et al. |
| 5,834,561 A | 11/1998 | Fukumoto et al. |
| 5,849,822 A | 12/1998 | Kido et al. |
| 5,886,098 A | 3/1999 | Ueda et al. |
| 5,967,714 A | 10/1999 | Ottersbach et al. |
| 5,997,815 A | 12/1999 | Anders et al. |
| 6,022,553 A | 2/2000 | Anders et al. |
| 6,039,940 A | 3/2000 | Perrault et al. |
| 6,045,919 A | 4/2000 | Alex et al. |
| 6,050,979 A | 4/2000 | Haemmerle et al. |
| 6,090,459 A | 7/2000 | Jadamus et al. |
| 6,096,800 A | 8/2000 | Ottersbach et al. |
| 6,103,368 A | 8/2000 | Fukuda et al. |
| 6,127,105 A | 10/2000 | Vandenabeele |
| 6,187,856 B1 | 2/2001 | Incorvia et al. |
| 6,194,530 B1 | 2/2001 | Klesse et al. |
| 6,197,322 B1 | 3/2001 | Dutkiewicz et al. |
| 6,203,856 B1 | 3/2001 | Ottersbach et al. |
| 6,207,361 B1 | 3/2001 | Greener et al. |
| 6,218,492 B1 | 4/2001 | Hill et al. |
| 6,242,526 B1 | 6/2001 | Siddiqui et al. |
| 6,248,811 B1 | 6/2001 | Ottersbach et al. |
| 6,251,967 B1 | 6/2001 | Perichaud et al. |
| 6,266,490 B1 | 7/2001 | Mukai et al. |
| 6,280,509 B1 | 8/2001 | Mallow |
| 6,319,883 B1 | 11/2001 | Graham et al. |
| 6,368,587 B1 | 4/2002 | Anders et al. |
| 6,410,040 B1 | 6/2002 | Melrose et al. |
| 6,428,866 B1 | 8/2002 | Jadamus et al. |
| 6,482,781 B2 | 11/2002 | Graham et al. |
| 6,497,868 B1 | 12/2002 | Tanahashi |
| 6,500,981 B1 | 12/2002 | Weipert |
| 6,525,134 B1 | 2/2003 | Lacroix et al. |
| 6,767,647 B2 | 7/2004 | Swofford et al. |
| 6,797,743 B2 | 9/2004 | McDonald |
| 7,491,753 B2 * | 2/2009 | Krishnan ..................... 523/122 |
| 2001/0007694 A1 | 7/2001 | Ottersbach et al. |
| 2001/0050478 A1 | 12/2001 | Schmitz |
| 2002/0037955 A1 | 3/2002 | Baumann et al. |
| 2002/0081923 A1 | 6/2002 | Artley et al. |
| 2002/0106413 A1 * | 8/2002 | Herbst et al. .................. 424/600 |
| 2002/0139583 A1 | 10/2002 | Masui et al. |
| 2002/0168473 A1 | 11/2002 | Ottersbach et al. |
| 2002/0177828 A1 | 11/2002 | Batich et al. |
| 2003/0013624 A1 | 1/2003 | Graham et al. |
| 2003/0017194 A1 | 1/2003 | Joerger et al. |
| 2003/0019813 A1 | 1/2003 | Ottersbach et al. |
| 2003/0022576 A1 | 1/2003 | Ottersbach et al. |
| 2003/0049437 A1 | 3/2003 | Devaney et al. |
| 2003/0068440 A1 | 4/2003 | Ottersbach et al. |
| 2005/0003163 A1 | 1/2005 | Krishnan |
| 2005/0065284 A1 | 3/2005 | Krishnan |
| 2005/0124724 A1 | 6/2005 | Burton et al. |
| 2005/0129766 A1 * | 6/2005 | Bringley et al. ............... 424/486 |
| 2006/0039939 A1 | 2/2006 | Lai et al. |
| 2008/0057049 A1 | 3/2008 | Krishnan |
| 2008/0182125 A1 * | 7/2008 | Krishnan et al. ............... 428/688 |
| 2008/0226584 A1 * | 9/2008 | Krishnan ................... 424/78.31 |
| 2008/0233062 A1 * | 9/2008 | Krishnan ........................ 424/59 |

FOREIGN PATENT DOCUMENTS

| | | |
|---|---|---|
| EP | 0000426 A1 | 1/1979 |
| EP | 0239213 A2 | 9/1987 |
| EP | 0252463 | 1/1988 |
| EP | 286009 A2 | 10/1988 |
| EP | 0204312 B1 | 8/1990 |
| EP | 0469196 A1 | 2/1992 |
| EP | 0290676 B1 | 8/1994 |
| EP | 747456 A2 | 12/1996 |
| EP | 1109845 | 6/2001 |
| GB | 1299012 | 12/1972 |
| GB | 2091277 A | 7/1982 |
| JP | 63-287543 | 11/1988 |
| NL | 7606306 | 12/1976 |
| WO | WO 91/12282 | 2/1991 |
| WO | WO 97/15603 | 5/1997 |
| WO | WO 97/45468 | 12/1997 |

(56) References Cited

FOREIGN PATENT DOCUMENTS

| WO | WO 98/51720 | 1/1998 |
| WO | WO 99/09837 | 3/1999 |
| WO | WO 00/05283 | 2/2000 |
| WO | WO 0008077 | 2/2000 |
| WO | PCT/US07/18838 | 2/2008 |
| WO | PCT/US07/018768 | 7/2008 |

* cited by examiner

CATIONIC LATEX AS A CARRIER FOR BIOACTIVE INGREDIENTS AND METHODS FOR MAKING AND USING THE SAME

REFERENCE TO RELATED APPLICATION

This application claims priority to U.S. Ser. No. 60/839,973, filed on Aug. 24, 2006, the contents of which are hereby incorporated by reference.

TECHNICAL FIELD OF THE INVENTION

This invention relates to the field of polymeric materials that can be used in combination with a wide variety of substrates, such as textiles, metal, cellulosic materials, plastics, and the like, and to the field of bioactive/antimicrobial agents such as antibacterial and antifungal materials.

BACKGROUND OF THE INVENTION

The deposition of latex polymer coatings on solid substrates has long been utilized to impart certain end-use performance properties to those substrates, such as hydrophobicity, strength, adhesive properties, compatibility, and the like. Depending upon the selection of the starting monomers, surfactants, emulsion polymerization conditions, and other parameters, the deposited polymers can be designed to carry an anionic, a cationic, or an amphoteric charge, a feature which directly influences coating performance. Further, the resulting latex polymer can be blended with a range of other functional materials to impart additional or enhanced features to the final coating material.

One particularly useful feature exhibited by cationic latex polymers disclosed in U.S. Patent Application Publication Number 2005/0003163 is their inherent antimicrobial characteristics. Cationic polymers can also be blended with compositions containing small molecule bioactive compounds, species more typically associated with antimicrobial activity, in order to enhance these properties. These antimicrobial components are usually employed in relatively small amounts as formulating ingredients that are added after the polymer has been made. While such blends are useful, many practical issues remain in attempts to enhance or control the extent of antimicrobial protection these compositions might afford. For example, such compositions and methods and are often inadequate for providing long-term protection of materials, especially in their antifungal properties. Methods to augment or to more finely control the antimicrobial properties are also needed. Regulatory issues associated with introducing a new antimicrobial material, namely the polymer, may be significant. Moreover, approaches to prolong or extend the effectiveness of the antimicrobial properties remain elusive.

Therefore, what are needed are new methods and approaches to impart and to enhance antimicrobial activity of latex polymers, as well as the coatings and articles prepared therefrom. What are also needed are methods to more closely manage the antimicrobial activity of such materials, including approaches to extend the effectiveness of their bioactivity.

SUMMARY OF THE INVENTION

This invention encompasses new methods and approaches to incorporate bioactive or antimicrobial ingredients such as antibacterial and antifungal agents into a latex, such that the antimicrobial properties of the latex can be enhanced and controlled. The present invention also relates to new types of bioactive cationic polymer latex materials. In one aspect, this disclosure provides a method for incorporating antimicrobial ingredients into a latex during the emulsion polymerization process. Previously, antimicrobial agents have been added to a latex after the polymerization process and in relatively small amounts as preservatives for the latex product or for the end use application such as paints. The present invention allows the use of higher concentrations of a wide range of bioactive ingredients, including highly hydrophobic bioactive ingredients, which can be readily incorporated into the latices such that the resulting latex particles function as carriers for the active ingredients. The thorough incorporation of an active ingredient in this manner can afford a substantially homogeneous distribution of the additive and result in superior and sustained performance compared to pre-made dispersions.

In one aspect of this invention, the emulsion polymerization is carried out such that the bioactive agents are incorporated into the polymer during the emulsion polymerization, typically by dissolving the bioactive component in a monomer stream. In this manner, the bioactive agents can be at least partially encapsulated within the latex polymer matrix. One advantage provided by this process is the ability to incorporate or encapsulate large amounts of bioactive ingredients, including hydrophobic components, without substantially degrading the bioactive agent. In another aspect, this invention also provides a tunable antimicrobial system based on a cationic latex that has some inherent antimicrobial properties, which also function as a carrier for at least one bioactive ingredient, and optionally further including another bioactive additive that can be blended with the latices disclosed herein. Thus, these latices can have a multifunctional purpose such as providing binding, strength, and dispersion properties in addition to being a carrier for an active functional ingredient, and optionally constituting one component of a blended antimicrobial composition.

In one aspect, because the bioactive ingredients are typically incorporated into a latex during the emulsion polymerization process, these bioactive components can be at least partially encapsulated within the latex polymer matrix. In another aspect, the bioactive components can be substantially encapsulated within the latex polymer matrix. While not intending to be bound by theory, it is believed that, by delivering the active ingredient to a desired end use application, the latex polymer with the encapsulated bioactive ingredients can provide sustained and controlled exposure of the bioactive ingredients to the environment in which they are deployed, thereby providing longer and more effective protection to the product or the application. Moreover, because the bioactive cationic latices can be formed by existing emulsion polymerization processes, the polymerization methods advantageously allow for the preparation of high molecular weight polymers.

In a further aspect, the methods disclosed herein also provide the potential to adjust the antimicrobial behavior using a combination of approaches to deploy the antimicrobial agent. For example, highly tailored antimicrobial properties can be imparted to a product by both incorporating the bioactive ingredient into a latex during the emulsion polymerization process, and by combining the resulting latex product with the same or different bioactive component in a blend. This approach allows antimicrobial properties to be selected and adjusted using the polymer, the additive, or both, depending on the circumstances and the performance required.

In yet a further aspect, the techniques disclosed herein can provide the ability to encapsulate larger amounts of the active ingredient into a latex composition than are afforded by standard methods. For example, antimicrobial components are usually employed in relatively small amounts as formulating ingredients once the latex polymer has been prepared, and such bioactives typically are utilized at concentrations ranging up to about 1000-2000 ppm. In contrast, the antimicrobial component of the latex compositions of this invention can be utilized in concentrations as high as about 40 weight percent based on the total monomer weight. In this aspect, this invention can provide stable, concentrated dispersions that can be used as such, or as an additive, or concentrated dispersions that can be diluted and added to other systems which require antimicrobial protection. High antimicrobial component concentrations provide flexibility and ensure the utility of these latex compositions as concentrates as well as in non-concentrated form.

While the methods disclosed herein can be applied to any bioactive agent that a particular end use requires, the present disclosure is primarily drawn to providing or enhancing the antimicrobial properties of a latex, substrate, or particular end product. The relevant antimicrobial activity can include antibacterial activity, antifungal activity, antiviral activity, antiparasitic activity, or any combination thereof, depending upon the particular selection of bioactive agents. As used herein, the general term "bioactive" component, agent, or ingredient is used interchangeably with the term "antimicrobial" component, agent, or ingredient.

In another aspect, this invention provides a bioactive cationic polymer latex comprising:
a) a latex polymer comprising the polymerization product of: i) at least one ethylenically unsaturated first monomer; and ii) at least one ethylenically unsaturated second monomer that is cationic or a precursor to a cation;
b) at least one bioactive component at least partially encapsulated within the latex polymer; and
c) optionally, at least one sterically bulky component incorporated into the latex polymer.

In this aspect, a wide range of weight percentages of ethylenically unsaturated first monomer and ethylenically unsaturated second monomer that is cationic or a precursor to a cation, which can be referred to as the "cationic" monomer, can be used. For example, the latex can comprise from about 0.01 to about 75 weight percent of the cationic second monomer based on the total monomer weight.

Also in this aspect, while the at least one sterically bulky component incorporated into the latex polymer is an optional component, this invention also provides for use of a wide range of amounts and concentrations of this component. Thus, as will be understood by the skilled artisan, in bioactive cationic polymer latices that do not incorporate at least one sterically bulky component, latex stability can be enhanced by increasing the relative proportion of the cationic second monomer, by the addition of surfactants such as nonionic surfactants, and the like, including any combination of such methods. The relative proportion of the cationic second monomer can be reduced and/or surfactants can be eliminated in the presence of at least one sterically bulky component.

Further, the latices of this invention can also comprise a sterically bulky component which is incorporated into the cationic polymer latex to sterically stabilize the latex. These sterically bulky components can include, but are not limited to, monomers, polymers, and mixtures thereof as set forth below. Thus, a monomer can be incorporated as a co-monomer that can attach to, or constitute a portion of the backbone of the cationic polymer, examples of which include an alkoxylated ethylenically unsaturated third monomer. A polymer can be incorporated by adsorbing or being grafted onto the latex surface, an example of which includes polyvinyl alcohol.

In still another aspect, this invention provides a method of making a bioactive cationic polymer latex comprising initiating an emulsion polymerization of an aqueous composition comprising, at any time during the emulsion polymerization:
a) at least one ethylenically unsaturated first monomer;
b) at least one ethylenically unsaturated second monomer that is cationic or a precursor to a cation;
c) at least one bioactive component;
d) at least one free-radical initiator;
e) optionally, at least one sterically bulky ethylenically unsaturated third monomer;
f) optionally, at least one sterically bulky polymer; and
g) optionally, at least one nonionic surfactant.

Thus, in one aspect, the at least one bioactive component can be dissolved in the monomer feed at any time during the emulsion polymerization process. Further, in another aspect, the aqueous composition components and the at least one bioactive component can be provided as a dispersion prior to initiating the emulsion polymerization. Thus, this invention provides for batch processes, in which the at least one bioactive component is present in the seed stage. In this aspect, the emulsion polymerization is initiated when all the components of the composition, including the at least one bioactive component, are present from the time of initiation. Further, this invention also provides for semi-continuous processes in which the emulsion polymerization is initiated at a time when all components of the composition are not present from the time of initiation, but some are added at various times after initiating the polymerization. In this aspect, for example, the at least one bioactive component can be added at any time after the seed stage. In another aspect, for example, any other component or combination of components provided above can be added at any time after the seed stage, except for at least a portion of the total amount of any component that is required to initiate and propagate an emulsion polymerization. Thus, the bioactive cationic latex provided herein can be made by any variety of batch or by a semi-continuous processes. For example, the at least one bioactive component can be provided as a dispersion and can be added to the composition during the emulsion polymerization process.

In one aspect, the bioactive latices of this invention can be provided or used as coatings, which can be applicable to medical implants, including artificial ball and socket joints, rods, stents, dental implants, pins, screws, catheters, and the like. Such coatings can also be provided on everyday surfaces, such as air-conditioning coils, air filters, pipes, roofing, bathroom items, kitchen items, and the like. Such a coating can prevent microbial infections, such as bacteria and mold, in vehicles as well as homes, hospitals, and other buildings. Further examples of uses of the resultant products are use as an aqueous solution or directly in powder form, for example, for sterilizing cooling-water circuits, or indirect use, for example by addition to paints or other surface coatings.

These and other features, aspects, embodiments, and advantages of the present invention will become apparent after a review of the following detailed description of the invention. It should be understood, however, that these aspects, embodiments, and examples are provided for illustrative purposes only, and are not to be construed in any way as imposing limitations upon the scope thereof.

DETAILED DESCRIPTION OF THE INVENTION

Figure 1:
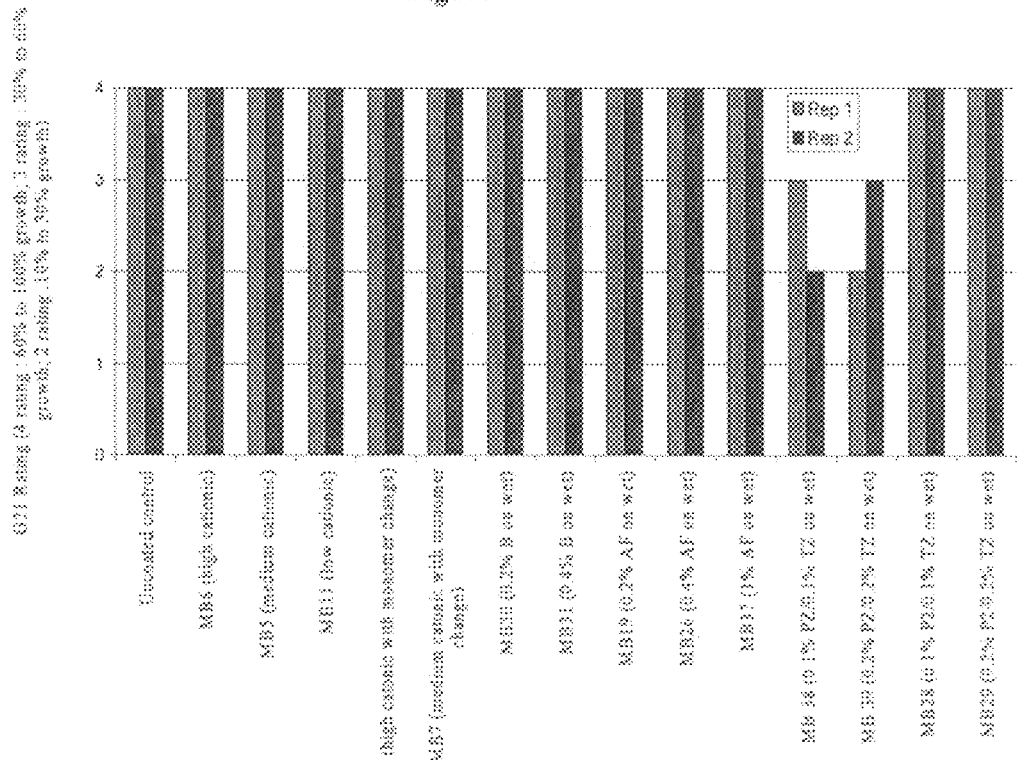
FIG. 1 is a graph showing the evaluation of the antimicrobial properties of various antimicrobial latexes, coated on Kraft paper, using ASTM G21.

The present invention provides new latex polymeric materials that can be used in combination with a wide variety of substrates, such as textiles, metal, cellulosic materials, plastics, and the like, in which the polymeric materials include bioactive components incorporated into the latex polymer. This invention also provides new methods and processes that allow incorporating high concentrations of an active ingredient such as antifungal agents during the emulsion polymerization. In one aspect, for example, the disclosed process can be used to incorporate from about 0.01 percent to about 40 percent, based on the total monomer weight ("phm" or parts per hundred of monomer), of a substantially hydrophobic bioactive ingredient during the emulsion polymerization. While the bioactive ingredient can be introduced at any stage during the polymerization process including very early during the seed formation stage, in one aspect, the bioactive component or additive (bioadditive) can be added during the later stages of polymerization process, for example, when from about 30 percent to about 90 percent of the monomer has been fed into the polymerization reactor.

Useful bioactive additives can be solids, liquids, or combinations thereof. Many of the bioactive additives that can be employed in this invention are substantially water insoluble or have limited solubility in water. In this aspect, the typical water insoluble, hydrophobic bioactive agent can be soluble in at least one of the monomers employed in the emulsion polymerization. Thus, the typical hydrophobic bioactive ingredient can be introduced into the polymerization reactor by substantially or partially dissolving it in a monomer feed at the appropriate time. Therefore, the typical ingredients chosen for imparting antimicrobial properties usually will be soluble in the monomers that are used to make the polymer latex. In another aspect, useful bioactive additives in this invention can also be substantially water soluble, examples of which include o-phenylphenate (deprotonated o-phenylphenol), and similar agents. In this aspect, it is not necessary that such a hydrophilic bioactive additive be soluble in any monomer that is to be polymerized.

In another aspect, it is not required that antimicrobial ingredients be soluble in at least one of the monomers used, as these ingredients can also be added as a pre-made dispersion in water. In this aspect, the dispersions can be made, among other ways, by using a relatively concentrated amount of the additive and dispersing by using surfactants, dispersants, and the like, and typically employing a mixing device such as a high speed mixer, a homogenizer, an Eppenbach mixer, or similar devices. In such a case, the dispersion can be fed into the reactor to deliver the appropriate amount of active ingredient into the latex.

In one aspect, this invention encompasses a bioactive cationic polymer latex comprising:
 a) a latex polymer comprising the polymerization product of: i) at least one ethylenically unsaturated first monomer; and ii) at least one ethylenically unsaturated second monomer that is cationic or a precursor to a cation;
 b) at least one bioactive component at least partially encapsulated within the latex polymer; and
 c) optionally, at least one sterically bulky component incorporated into the latex polymer.

As provided herein, the at least one sterically bulky component incorporated into the latex polymer can be selected independently from at least one sterically bulky ethylenically unsaturated third monomer, at least one sterically bulky polymer, or any combination thereof. Each of these components, as well as optional or additional components, is considered herein.

In another aspect, this invention also encompasses a method of making a bioactive cationic polymer latex comprising initiating an emulsion polymerization of an aqueous composition comprising, at any time during the emulsion polymerization:
 a) at least one ethylenically unsaturated first monomer;
 b) at least one ethylenically unsaturated second monomer that is cationic or a precursor to a cation;
 c) at least one bioactive component;
 d) at least one free-radical initiator;
 e) optionally, at least one sterically bulky ethylenically unsaturated third monomer;
 f) optionally, at least one sterically bulky polymer; and
 g) optionally, at least one non nonionic surfactant.

In yet another aspect, this invention provides a method of making a bioactive cationic polymer latex comprising
 a) providing an aqueous composition comprising:
  i) at least one ethylenically unsaturated first monomer;
  ii) at least one ethylenically unsaturated second monomer that is cationic or a precursor to a cation;
  iii) optionally, at least one sterically bulky ethylenically unsaturated third monomer;
  iv) at least one free-radical initiator; and
  v) optionally, at least one non-ionic surfactant;
 b) initiating an emulsion polymerization of the composition; and
 c) adding at least one bioactive component to the composition during the emulsion polymerization process.

Many compounds and species that can be used as ethylenically unsaturated first monomers, ethylenically unsaturated second monomers, and sterically bulky components are disclosed in the European Patent Number EP 1109845 and the corresponding PCT Published Patent Application WO 00/8008077, each disclosure of which is incorporated herein by reference in its entirety.

Ethylenically Unsaturated First Monomers

Various ethylenically unsaturated first monomers can be used in the latex of the present invention. In one aspect, ethylenically unsaturated first monomers can be non-cationic. Examples of suitable monomers can be found at least in U.S. Pat. No. 5,830,934, U.S. Patent Application Publication Numbers 2005/0065284 and 2005/0003163, and European Patent Number EP 1109845, all to Krishnan, each disclosure of which is incorporated herein by reference in its entirety. In this aspect, examples of such monomers include, but are not limited to, vinyl aromatic monomers, halogenated or non-halogenated olefin monomers, aliphatic conjugated diene monomers, non-aromatic unsaturated mono- or dicarboxylic ester monomers, monomers based on the half ester of an unsaturated dicarboxylic acid monomers, unsaturated monoor dicarboxylic acid monomers, nitrogen-containing monomers, nitrile-containing monomers, cyclic or acyclic amine-containing monomer, branched or unbranched alkyl vinyl ester monomers, halogenated or non-halogenated alkyl acrylate monomers, halogenated or non-halogenated aryl acrylate monomers, carboxylic acid vinyl esters, acetic acid alkenyl esters, carboxylic acid alkenyl esters, a vinyl halide, a vinylidene halide, or any combination thereof, any of which having up to 20 carbon atoms. In this aspect, it is the Applicant's intent to disclose acrylate and methacrylate moieties when either moiety is disclosed in a suitable monomer. Thus, the disclosure that an acrylate monomer is a suitable ethylenically unsaturated first monomer also encompasses the disclosure that the corresponding methacrylate monomer is also a suitable first monomer. The abbreviation (meth)acrylate can be used to represent such a disclosure.

Many different ethylenically unsaturated first monomers can be used in preparing the bioactive latices of this invention. In one aspect, suitable examples of ethylenically unsaturated first monomers include, but are not limited to, styrene, para-methyl styrene, chloromethyl styrene, vinyl toluene, ethylene, butadiene, methyl (meth)acrylate, ethyl (meth)acrylate, propyl (meth)acrylate, butyl (meth)acrylate, pentyl (meth)acrylate, glycidyl (meth)acrylate, isodecyl (meth)acrylate, lauryl (meth)acrylate, monomethyl maleate, itaconic acid, (meth)acrylonitrile, (meth)acrylamide, N-methylol (meth)acrylamide, N-(isobutoxymethyl)(meth)acrylamide, vinyl neodecanoate, vinyl versatates, vinyl acetate, $C_3$-$C_8$ alkyl vinylethers, $C_3$-$C_8$ alkoxy vinyl ethers, vinyl chloride, vinylidene chloride, vinyl fluoride, vinylidene fluoride, trifluoroethylene, tetrafluoroethylene, chlorotrifluoroethylene, hexafluoropropylene, chlorotrifluoroethylene, perfluorobutyl ethylene, perfluorinated $C_3$-$C_8$ alpha-olefins, fluorinated $C_3$-$C_8$ alkyl vinylethers, perfluorinated $C_3$-$C_8$ alkyl vinylethers, perfluorinated $C_3$-$C_8$ alkoxy vinyl ethers, and the like, or any combination thereof. Thus, halogenated analogs of suitable ethylenically unsaturated first monomers are encompassed by this disclosure, and it is Applicant's intent to disclose any and all suitable halogen-substituted analogs or derivatives of these monomers, including fluorine-substituted analogs, chlorine-substituted analogs, bromine-substituted analogs, and iodine-substituted analogs. The term "halogen-substituted" is meant to include partially halogen substituted and perhalogen substituted, in which any halogen substituents can be the same or can be different. In this aspect as well, it is the Applicant's intent to disclose both acrylate and methacrylate moieties when either moiety is disclosed in a suitable monomer.

In another aspect, the ethylenically unsaturated first monomer can be halogenated or can be non-halogenated. Similarly, the ethylenically unsaturated first monomer can be fluorinated or can be non-fluorinated. For example, fluorinated analogs of alkyl acrylates or methacrylates can be used, as well as the non-fluorinated compounds. The ethylenically unsaturated first monomer can also be chlorinated or can be non-chlorinated. The ethylenically unsaturated first monomer can also be brominated or can be non-brominated. The ethylenically unsaturated first monomer can also be iodinated or can be non-iodinated. For example, fluorinated analogs of alkyl acrylates or methacrylates can be used, as well as the non-fluorinated compounds.

In yet another aspect of this invention, the latices provided herein can comprise from about 20 percent to about 99.5 percent by weight of the ethylenically unsaturated first monomer, based on the total monomer weight. In this aspect, the latex of this invention can also comprise from about 30 percent to about 99 percent, from about 40 percent to about 97 percent, from about 50 percent to about 95 percent, from about 60 percent to about 90 percent, or from about 70 percent to about 90 percent by weight of the ethylenically unsaturated first monomer, based on the total monomer weight. In this aspect, the Applicant's intent is to disclose individually each possible number that such ranges could reasonably encompass, as well as any sub-ranges and combinations of sub-ranges encompassed therein. In this aspect, as understood by the skilled artisan, the particular chemical and physical properties of a specific monomer will have a bearing on the range of weight percentages most suitable for that monomer.

Ethylenically Unsaturated Cationic Second Monomers

In still another aspect, the latex polymer of the present invention also comprises the polymerization product of at least one ethylenically unsaturated second monomer that is cationic or a precursor to a cation. As provided herein, the at least one ethylenically unsaturated second monomer that is cationic or a precursor to a cation can be collectively referred to by the term "cationic monomer," that is, any monomer which possesses or can be made to posses a positive charge. In one aspect, this positive charge may be imparted by the presence of a heteroatom in the monomer, such as nitrogen, that can constitute the site of attachment of a proton or any other cationic Lewis Acid that would impart a positive charge to the monomer. For example, quaternary amine monomers can be used as a "cationic monomer" in the latex of the invention, which includes quaternary amine monomers obtained from any neutral amine monomer disclosed herein by, for example, protonation using an acid or by alkylation using an alkyl halide. Exemplary heteroatoms include, but are not limited to, nitrogen, sulfur, phosphorus, and the like. Thus, the cationic monomer is typically incorporated into the latex polymer by virtue of its ethylenic unsaturation.

Examples of suitable cationic monomers can be found at least in U.S. Patent Application Publication Numbers 2005/0065284 and 2005/0003163, to Krishnan. In this aspect, examples of cationic monomers include, but are not limited to, an amine monomer, an amide monomer, a quaternary amine monomer, a phosphonium monomer, a sulfonium monomer, or any combination thereof, any of which having up to 20 carbon atoms. Further, suitable examples of ethylenically unsaturated cationic monomers that can be used in the latex of the present invention include, but are not limited to, dimethylaminoethyl acrylate; diethylaminoethyl acrylate; dimethyl aminoethyl methacrylate; diethylaminoethyl methacrylate; tertiary butylaminoethyl methacrylate; N,N-dimethyl acrylamide; N,N-dimethylaminopropyl acrylamide; acryloyl morpholine; N-isopropyl acrylamide; N,N-diethyl acrylamide; dimethyl aminoethyl vinyl ether; 2-methyl-1-vinyl imidazole; N,N-dimethyl-aminopropyl methacrylamide; vinyl pyridine; vinyl benzyl amine; dimethylaminoethyl acrylate, methyl chloride quarternary; dimethylaminoethyl methacrylate, methyl chloride quarternary; diallyldimethylammonium chloride; N,N-dimethylaminopropyl acrylamide, methyl chloride quaternary; trimethyl-(vinyloxyethyl) ammonium chloride; 1-vinyl-2,3-dimethylimidazolinium chloride; vinyl benzyl amine hydrochloride; vinyl pyridinium hydrochloride; or any combination thereof. While these listed examples include both free base compounds, and various quarternary salts such as hydrochloride or methyl chloride quarternary salts, any suitable Lewis acid that imparts a positive charge to the monomer can be used to form the cationic monomers of this disclosure.

In a further aspect, other amines or amine salts can also be used as ethylenically unsaturated second monomers to prepare the latex polymer of the present invention. For example, various amine salts can be obtained, for example, by the reaction of an epoxy group with a secondary amine and the subsequent neutralization of the newly formed tertiary amine with an acid. For example, the reaction of glycidyl methacrylate with a secondary amine can be carried out and the product can be free radically polymerized. Quaternary amine functionality can also be generated as a "post-reaction" on a preformed polymer having, for example, an epoxy group. Examples of such reactions are described in the article, "Polymer Compositions for Cationic Electrodepositable Coatings," Journal of Coatings Technology, Vol 54, No 686, March 1982, which is incorporated herein by reference in its entirety. It should also be appreciated that cationic functionality can also be imparted using sulfonium or phosphonium chemistry, examples of which are described in this reference, as will be appreciated by one of ordinary skill in art.

In a further aspect, the latex polymer of this invention can comprise from about 0.01 to about 75 percent by weight of the ethylenically unsaturated second monomer that is cationic or a precursor to a cation, based on the total monomer weight. In this aspect, the latex of this invention can also comprise from about 0.025 to about 70 percent, from about 0.05 to about 60 percent, from about 0.1 to about 50 percent, from about 0.25 to about 40 percent, from about 0.5 to about 30 percent, from about 1 to about 20 percent, or from about 1.5 to about 15 percent, by weight of the cationic second monomer, based on the total monomer weight. In this aspect, the Applicant's intent is to disclose individually each possible number that such ranges could reasonably encompass, as well as any sub-ranges and combinations of sub-ranges encompassed therein.

Sterically Bulky Components

As disclosed herein, one aspect of this invention encompasses a cationic polymer latex comprising: a) a latex polymer as disclosed herein; b) at least one bioactive component at least partially encapsulated within the latex polymer; and c) optionally, at least one sterically bulky component incorporated into the latex polymer. The at least one sterically bulky component incorporated into the latex polymer can be selected independently from at least one sterically bulky ethylenically unsaturated third monomer, at least one sterically bulky polymer, or any combination thereof. In this aspect, and while not intending to be bound by theory, this sterically bulky component is typically incorporated into the cationic polymer latex to sterically stabilize the latex.

As used herein, the term "incorporated" with respect to the use of the at least one sterically bulky ethylenically unsaturated third monomer includes, but is not limited to, the attachment of this third monomer to the cationic polymer, for example, by co-polymerization of the third monomer with the first monomer and second cationic monomer disclosed herein, to form the cationic polymer latex. Further, the term "incorporated" with respect to the at least one sterically bulky ethylenically unsaturated third monomer can also include the attachment of this third monomer to the cationic polymer in any other fashion, such as, for example, by grafting onto the polymer backbone. In another aspect, the term "incorporated" with respect to the use of the at least one sterically bulky polymer includes, but is not limited to, the attachment or association of this polymer into the latex for methods including, but not limited to, adsorbing or grafting the sterically bulky polymer onto the latex surface. For example, polyvinyl alcohol can be incorporated into the latex in this manner. This sterically stabilizing component can encompass a nonionic monomer or nonionic polymer which incorporate steric stabilization to the latex particle without affecting the deposition characteristics of the cationic polymer latex.

Exemplary monomers that can be used as sterically bulky ethylenically unsaturated third monomers include, but are not limited to, those ethylenically unsaturated monomers that contain alkoxylated (for example, ethoxylated or propoxylated) functionalities. In one aspect, examples of such monomers include, but are not limited to, at least one a sterically bulky ethylenically unsaturated compound selected independently from the following:

a) $CH_2=C(R^{1A})COO(CH_2CHR^{2A}O)_m R^{3A}$, wherein $R^{1A}$, $R^{2A}$, and $R^{3A}$ can be selected independently from H or an alkyl group having from 1 to 6 carbon atoms, inclusive, and m can be an integer from 1 to 30, inclusive. In this aspect, $R^{1A}$, $R^{2A}$, and $R^{3A}$ can also be selected independently from H or methyl, m can be an integer from 1 to 10, inclusive;

b) $CH_2=C(R^{1B})COO(CH_2CH_2O)_n(CH_2CHR^{2B}O)_p R^{3B}$, wherein $R^{1B}$, $R^{2B}$, and $R^{3B}$ can be selected independently from H or an alkyl group having from 1 to 6 carbon atoms, inclusive, and n and p can be integers selected independently from 1 to 15, inclusive. Also in this aspect, $R^{1B}$, $R^{2B}$, and $R^{3B}$ can be selected independently from H or methyl, and n and p can be integers selected independently from 1 to 10, inclusive;

c) $CH_2=C(R^{1C})COO(CH_2CHR^{2C}O)_q(CH_2CH_2O)_r R^{3C}$, wherein $R^{1C}$, $R^{2C}$, and $R^{3C}$ can be selected independently from H or an alkyl group having from 1 to 6 carbon atoms, inclusive, and q and r can be integers selected independently from 1 to 15, inclusive. Further to this aspect, $R^{1C}$, $R^{2C}$, and $R^{3C}$ can be selected independently from H or methyl, and q and r can be integers selected independently from 1 to 10, inclusive; or d) any combination of any of these compounds.

In another aspect of this invention, a number of other types of unsaturated compounds can be used as sterically bulky ethylenically unsaturated third monomers include, but are not limited to, polymerizable surfactants. Thus, further examples of suitable sterically bulky ethylenically unsaturated third monomers include, but are not limited to, alkoxylated monoesters of a dicarboxylic acid; alkoxylated diesters of a dicarboxylic acid; polyoxyethylene alkylphenyl ethers such as NOIGEN RN™; or any combination thereof. In this aspect, for example, ethoxylated mono- and diesters of diacids such as maleic and itaconic acids can also be used to achieve the desired stabilizing effect. Acrylate, methacrylate, vinyl and allyl analogs of surfactants, referred to as polymerizable surfactants, can also be used in this manner. Examples of such polymerizable surfactants include, but are not limited to, TREM LF-40™ sold by Cognis. In one aspect, these surfactants are typical in that they possess ethylenic unsaturation that allows the surfactants to be incorporated into the latex polymer itself, as well as possessing hydrophobic and hydrophilic functionality that varies. In another aspect, surfactants that are particularly applicable to the present invention include the nonionic surfactants, wherein the hydrophilic character is believed to be attributable to the presence of alkylene oxide groups. Examples of suitable nonionic surfactants include, but are not limited to, ethylene oxide, propylene oxide, butylene oxide, and the like. In such species, the degree of hydrophilicity can vary based on the selection of functionality.

The at least one sterically bulky component incorporated into the latex polymer can also constitute at least one polymer. Again, while not intending to be bound by theory, it is thought that such polymers provide steric stability to the resulting latex polymer. Such polymers are sometimes referred to in the art as protective colloids. Examples of sterically bulky polymers include, but are not limited to, polyvinyl alcohols, polyvinyl pyrollidone, hydroxyethyl cellulose, and the like, including any combination of these materials. Moreover, mixtures or combinations of any of the aforementioned sterically bulky monomers and any of these sterically bulky polymers can also be used as the at least one sterically bulky component that is incorporated into the latex polymer. A number of other monomers and polymers that can be used in the present invention that can impart stability are provided in U.S. Pat. No. 5,830,934 to Krishnan et al., the entirety of which is incorporated herein by reference.

The optional at least one sterically bulky component can be present in an amount ranging from 0 to about 25 percent by weight, based on the total weight of the monomers. In this aspect, the latex of this invention can also comprise from about 0.1 to about 20 percent, from about 0.2 to about 18 percent, from about 0.5 to about 15 percent, from about 0.7 to about 12 percent, or from about 1 to about 10 percent by weight of the sterically bulky component, based on the total monomer weight. In this aspect, the Applicant's intent is to disclose individually each possible number that such ranges could reasonably encompass, as well as any sub-ranges and combinations of sub-ranges encompassed therein.

Free Radical Initiators

In still a further aspect, the latex of the present invention can include a free radical initiator, the selection of which is known to one of ordinary skill in the art. Thus, while any polymerization initiator whether it is cationic or anionic in nature can be used as a polymerization initiator, for example, persulfates, peroxides, and the like, typical initiators are azo-based compounds and compositions. Moreover, in this aspect, for producing a cationic latex, any free radical initiator which generates a cationic species upon decomposition and contributes to the cationic charge of the latex can be utilized. Examples of such an initiator include, but are not limited to, is 2,2'-azobis(2-amidinopropane)dihydrochloride), which is sold commercially as WAKO V-50™ by Wako Chemicals of Richmond, Va.

Bioactive/Antimicrobial Agents and Their Incorporation

The cationic latex polymerization and encapsulation method disclosed herein can be utilized with a wide range of antimicrobial agents. Cationic latex has proved very useful due, in part, to the inherent antimicrobial attributes of the cationic polymer which can be supplemented with at least one antimicrobial agent. In this aspect, this invention also provides methods to prepare an antifungal fortified cationic latex and to deposit such a latex through a wet end process onto pulp fibers, such that the resultant sheet of paper is substantially antifungal. This method, which includes deposition onto pulp fibers, highlights the utility of this process that incorporates an antimicrobial active ingredient into a resulting cationic latex for deposition, in part, because the process is facilitated by opposite charges on the pulp fibers and the cationic latex. This opposite charge features typically leads to substantial uniformity of deposition of the cationic latex on the fiber and a substantially homogeneous product. In this aspect, the typical initiators also include azo-based compounds and compositions.

As provided herein, a wide range of polymerization conditions can be used. In one aspect, the bioactive component or additive is typically soluble in at least one of the monomers employed, and/or soluble in a monomer mixture or composition used. In another aspect, the bioactive additive can be introduced at any stage during the polymerization process including very early during the seed formation stage, including initiating the emulsion polymerization when all the components of the composition, including the at least one bioactive component, are present at the time of initiation. In another aspect, the bioadditive can be added during a later stage of polymerization process. For example, the bioactive ingredient can be introduced into the monomer feed when about 30 percent of the monomer has been fed into the polymerization reactor.

While not intending to be bound by theory, it is believed that introducing the bioactive component into the monomer feed relatively late in the polymerization process could help minimize degradation of the bioactive agent arising from the polymerization conditions. For example, it is possible that the bioactive agent could be degraded at the temperature under which polymerization is conducted, or could react with certain monomers or other components. Accordingly, to minimize any such degradation process, the bioactive agent can be added at such a time in the process, for example, when the process is more than about 50%, more than about 60%, more than about 70%, more than about 80%, or more than about 90% complete, thus minimizing the contact time between the bioactive agent and other components under the polymerization conditions. Another approach to minimize degradation of the bioactive agent is to employ bioactive agents that comprise "latent" bioactive moieties that can be activated by thermal, chemical, photochemical, or similar means, at a suitable time after the emulsion polymerization.

In another aspect of this invention, the bioactive additive can be introduced at any stage during an emulsion polymerization process, including, for example at such a time during the process at which the resulting antimicrobial latex exhibits a bioactivity that is not substantially diminished relative to a standard bioactivity exhibited by the same antimicrobial latex prepared by adding the bioactive component when the emulsion polymerization is about 50% complete. Thus, this standard bioactivity is the activity of the same antimicrobial latex synthesized from the same bioactive component and the same latex at substantially the same concentrations, prepared by adding the bioactive component when the emulsion polymerization is about 50% complete, as evaluated under similar conditions. The term "not substantially diminished" is used to refer to any difference in activity of the resulting bioactive latex, relative to this standard bioactivity, that meets any one, or more than one, of the following criteria: 1) the measured activity of the resulting bioactive latex is less than or equal to about 15% lower than the measured activity of the standard; 2) the activity of the resulting bioactive latex has a numerical activity rating based on an arbitrary activity scale that is less than or equal to about 35% lower than the numerical activity rating of the standard; or 3) the empirically-based descriptive rating of the activity level of the resulting bioactive latex is no more than two descriptive rating levels lower than the activity rating level of the standard. The measurement of antimicrobial activity can be determined according to any one, or more than one, of the following test standards: ASTM E2180-01; ASTM E2149-01; ASTM E1882-05; ASTM D3273; AATCC Test Method 30, Part 3; AATCC Test Method 100; ASTM D5590. An example of criterion 1) of "not substantially diminished" is as follows. A bioactive additive can be introduced at a time, or introduction can be initiated at a time, during an emulsion polymerization process so as to provide a resulting antimicrobial latex having a minimum inhibitory concentration (MIC) of 0.009 mg/mL, which is less than 15% lower than a MIC of 0.010 mg/mL for the standard. An example of criterion 2) of "not substantially diminished" is as follows. The bioactive additive can be introduced at a time, or introduction can be initiated at a time, during an emulsion polymerization process so as to provide a resulting antimicrobial latex having numerical activity rating of bioactivity based on an arbitrary activity scale of 5, which is less than 35% lower than the numerical activity rating of bioactivity of 7 for the standard. An example of criterion 3) of "not substantially diminished" is as follows. In an empirically-based descriptive rating system that includes contiguous rating levels of "excellent activity," "very good activity," and "good activity," the bioactive additive can be introduced at a time, or introduction can be initiated at a time, during an emulsion polymerization process so as to provide a resulting antimicrobial latex having an activity rating of "good activity," as compared to an activity rating of "excellent activity" for the standard. In any of these measurements of activity, the bioactive additive can be introduced at any time during the polymerization process that provides this result, or introduction can be initiated at a time during the polymerization process that provides the result disclosed above.

In another aspect, it is not necessary to introduce the bioactive component into the monomer feed relatively late in the polymerization process. For example, the bioadditive agent can also be added when about 0 percent, about 10 percent, about 20 percent, about 30 percent, about 40 percent, about 50 percent, about 60 percent, about 70 percent, about 80 percent, about 90 percent, or about 100 percent of the monomer has been fed into the polymerization reactor. In this aspect, the emulsion polymerization is initiated at a time when all components of the composition are not present from the time of initiation, but some are added at various times after initiating the polymerization, including, but not limited to, the at least one bioactive component. Also in this aspect, the Applicant's intent is to disclose any and all ranges between such numbers, and to claim individually each possible number that such ranges could reasonably encompass, as well as any sub-ranges and combinations of sub-ranges encompassed therein.

In another aspect, polymerization can be effected at a range of temperatures, typically selected between the lowest temperature that affords reasonable polymerization rates, and the highest temperature allowable that does not result in substantial degradation or decomposition of the antimicrobial bioactive ingredient. In one aspect, the polymerization can be carried out at the lowest temperature possible such that polymerization proceeds. In this case, the polymerization temperature should be sufficiently low to not substantially degrade or decompose any bioactive ingredient that is incorporated, yet high enough such that polymerization rates and times are adequate for useful production of the final latex polymer.

The antimicrobial agent can also be fed as a pre-emulsion made by emulsifying a mixture of monomer, additive, surfactants, water, and the like, using methods and materials known to one of ordinary skill in the art. For example, In this aspect, the dispersions can be made, among other ways, by using a relatively concentrated amount of the additive and dispersing by using surfactants, dispersants, and the like, and typically employing a mixing device such as a high speed mixer, a homogenizer, an Eppenbach mixer, or similar devices. Moreover, any other conceivable process or process known to one of ordinary skill that provides emulsion polymers in which the additive is a dispersion, an emulsion, a suspension, or the like, or substantially dissolved in the monomer mixture prior to polymerization, can be utilized.

In one aspect, useful antimicrobial agents that provide antifungal and antibacterial properties can be, in many cases, susceptible to oxidation or reduction, especially when exposed to higher temperatures. Therefore in addition to antimicrobial agent solubility, another aspect of selecting and incorporating antimicrobial agents is diminishing any oxidation or reduction reaction that would degrade such components. The processes of this invention can typically achieve this result by controlling the polymerization temperature, adjusting the time period that the active ingredient is added into the reaction to control exposure to the polymerization temperature, by adding an appropriate oxidant or reductant at some time during the polymerization to diminish or moderate any redox degradation, or any combination of these methods.

In a further aspect of the present invention, the at least one bioactive component can be selected independently from undecylenic acid; undecylenic alcohol; the reaction product of undecylenic acid with hydroxylethyl (meth)acrylate or polyethylene glycol (meth)acrylate; the reaction product of undecylenic alcohol with (meth)acrylic acid, maleic anhydride, or itaconic acid; chitosan or modified chitosans; or any combination thereof. Additional antimicrobial components that can be used in the present invention are provided in U.S. Patent Application Publication Number 2005/0003163, to Krishnan, which is incorporated herein by reference in its entirety. Another aspect of this invention provides that the at least one bioactive component can be selected independently from copper, copper salts, silver, silver salts, zinc, zinc salts, silver oxide, zinc oxide, chlorhexidine, chlorhexidine gluconate, glutaral, halazone, hexachlorophene, nitrofurazone, nitromersol, povidone-iodine, thimerosol, $C_1$- to $C_5$-parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, pyrithione salts, sodium pyrithione, zinc pyrithione, (dodecyl) (diethylenediamine) glycine, (dodecyl) (aminopropyl) glycine, phenol, m-cresol, o-cresol, p-cresol, o-phenyl-phenol, resorcinol, vinyl phenol, polymeric guanidines, polymyxins, bacitracin, circulin, octapeptins, lysozmye, lysostaphin, cellulytic enzymes, vancomycin, ristocetin, actinoidins, avoparcins, tyrocidin A, gramicidin S, polyoxin D, tunicamycin, neomycin, streptomycin, or any combination thereof.

Yet another aspect of this invention provides that the at least one bioactive component can exhibit fungicidal activity. In this aspect, suitable fungicides that are applicable to this disclosure include, but are not limited to, azoles, quaternary ammonium compounds, dithiocarbamates, dicarboximides, or any combination thereof. For example, in this aspect, an azole fungicide can be selected from azaconazole, biternatol, bromuconazole, cyproconazole, diniconazole, fenbuconazole, flusilazole, flutnafol, imazalil, imibenconazole, metconazole, paclobutrazol, perfuazoate, penconazole, simeconazole, triadimefon, triadimenol, uniconazole, or any combination thereof. Also in this aspect, a dithiocarbamate fungicide can be selected from mancozeb, maneb, metiram, zineb, or any combination thereof.

In another aspect, suitable fungicides can include, but are not limited to, fludioxonil, fluquinconazole, difenoconazole, 4,5-dimethyl-N-(2-propenyl)-2-(trimethylsilyl)-3-thiophenecarboxamide (sylthiopham), hexaconazole, etaconazole, triticonazole, flutriafol, epoxiconazole, bromuconazote, tetraconazole, myclobutanil, bitertanol, pyremethanil, cyprodinil, tridemorph, fenpropimorph, kresoxim-methyl, azoxystrobin, ZEN90160™, fenpiclonil, benalaxyl, furalaxyl, metalaxyl, R-metalaxyl, orfurace, oxadixyl, carboxin, prochloraz, triflumizole, pyrifenox, acibenzolar-S-methyl, chlorothalonil, cymoxanil, dimethomorph, famoxadone, quinoxyfen, fenpropidine, spiroxamine, triazoxide, BAS50001F™, hymexazole, pencycuron, fenamidone, guazatine, and the like, including any combination thereof. Still another aspect of this invention provides that suitable fungicides can include, but are not limited to, benomyl (also known as benlate), captan, carbendazim, capropamid, ethirimol, flutolanil, fosetyl-aluminum, fuberidazole, hymexanol, kasugamycin, iminoctadine-triacetate, ipconazole, iprodione, mepronil, metalaxyl-M (mefenoxam), nuarimol, oxine-copper, oxolinic acid, perfurazoate, propamocarb hydrochloride, pyroquilon, quintozene (also known as PCNB), silthiopham, MON™ 65500, tecnazene, thiabendazole, thifluzamide, thiophenate-methyl, thiram, tolclofos-methyl, triflumizole, and the like, including any combination thereof. Moreover any combination or mixture of any of these fungicides can be employed.

In yet another aspect of this invention, typical amounts of bioactive component that can be added during the emulsion polymerization can range from about 0.01 percent to about 40 percent by weight bioactive additive, based on the total monomer weight. In another aspect, typical amounts of bioactive component that can be added during the emulsion polymerization can range from about 0.025 percent to about 35 percent, from about 0.05 percent to about 30 percent, from about 0.1 percent to about 25 percent, from about 0.25 percent to about 20 percent, or from about 0.5 percent to about 15 percent by weight bioactive additive, based on the total monomer weight. In this aspect, the Applicant's intent is to disclose individually each possible number that such ranges could reasonably encompass, as well as any sub-ranges and combinations of sub-ranges encompassed therein. As compared to the amount of antimicrobial component added as a "post-add," these concentrations of bioactive additive are typically much larger than the post-add amounts. Among other things, this features provides stable, concentrated dispersions that can be used as concentrates, as additives, or as concentrated dispersions that can be diluted and added to other systems which require antimicrobial protection.

As disclosed herein, in one aspect, the bioactive component is typically dissolved in the monomer feed during the emulsion polymerization process. Thus, the bioactive additive is typically at least partially soluble in one or more of the monomers employed. Further, the bioactive additive can be moderately soluble, substantially soluble, or highly soluble in one or more of the monomers employed. This feature can allow, among other things, the incorporation of hydrophobic bioactive ingredients, the use of high amounts and concentrations of bioactive ingredients, greater control over the antimicrobial properties including enhancing the effectiveness of the antimicrobial properties, the use of minimal amounts of surfactant, and at least partial encapsulation of the bioactive ingredient. In some instances, the latex polymer can substantially encapsulate the added bioactive component, thus the latex polymer can function as a type of carrier for the active ingredients. This process also allows for the incorporation of the antimicrobial ingredients without substantially degrading the activity of these compounds.

In another aspect, useful bioactive additives in this invention can also be water soluble to any extent, including substantially water soluble, examples of which include o-phenylphenate (deprotonated o-phenylphenol), and similar agents. Thus, it is not necessary that such a hydrophilic bioactive additive be soluble in any monomer that is to be polymerized. In still another aspect, useful bioactive additives in this invention can be substantially insoluble in the monomers being polymerized and substantially insoluble in water. In this aspect, a dispersion of the bioactive component can be made by, among other ways, by dispersing a certain concentration of the additive with the use of surfactants and the like, typically with the use of high speed mixers or homogenizers.

Because the post-added additives are typically dispersions that are post-mixed into a formulation, it can be difficult to adequately disperse the bioactive additive into the polymer film, binder, coating, or the like, in which they are used. Moreover, typical additive dispersions that are used today can cause or be associated with moisture sensitivity and leaching of the additive, and many post-adds do not persist within the product for a sufficient period of time to provide adequate antifungal protection. The approach provided in this disclosure allows the use of minimal surfactants to incorporate the bioactive additives into the latex, and because the bioactives are introduced during the polymerization, they are typically encapsulated and are not easily released from the resulting latex. As a result, there can be less leaching of the bioactive component, and better overall distribution of the bioactive ingredient throughout the polymer film, binder, coating, and the like. Accordingly, this method can provide a potentially safer and more environmentally friendly dispersion, while also offering sustained antifungal or antibacterial protection.

The process disclosed herein also allows the latex to be used as a concentrate, in contrast to the typical concentrate dispersions that are not as stable as those provided herein. As a result, the typical concentrate dispersions are not as easily manipulated and therefore cannot be incorporated as easily into a finished product, and can have deleterious effects on performance, such as water sensitivity, if dosage is increased. A concentrate of the latex provided herein can be diluted and used with or without other materials if such materials are needed to provide an adequate level of additive. Intimate incorporation of an active ingredient in this manner can afford a homogeneous distribution of the additive and result in superior and sustained performance compared to a pre-made dispersions. An additional benefit of this intimate incorporation of the bioactive agent is apparent in films that are prepared using these latices, which are observed to be substantially transparent. This feature highlights the highly homogeneous assimilation of the bioactive agent into the latex particles and how this uniform distribution can provide useful properties for applications such as transparent bioactive films and the like.

Other Additives

In another aspect of this disclosure, the latex provided herein can also include other additives to improve the physical and/or mechanical properties of the polymer, the selection of which are known to one skilled in the art. Such additives include, for example, processing aids and performance aids, including but are not limited to, cross-linking agents, natural or synthetic binders, plasticizers, softeners, foam-inhibiting agents, froth aids, flame retardants, dispersing agents, pH-adjusting components, sequestering or chelating agents, or other functional components, or any suitable combination thereof.

Exemplary Substrates and Applications for Bioactive Cationic Polymer Latices

The deposition of the latex polymer coatings of this disclosure on any number of different substrates, such as textiles, metal, cellulosic materials, plastics, and the like, can impart desired end-use performance properties to those materials, and therefore tailor the substrates for a range of applications. For example, in one aspect, the present disclosure provides a treated fibrous material which can comprise at least one fiber and at least one bioactive cationic polymer latex as provided herein. In one aspect, the treated fibrous material can comprise at least one fiber and at least one bioactive cationic polymer latex deposited on, or associated with, the at least one fiber. If desired, the bioactive cationic polymer can be applied to the fiber in the form of a powder, or the polymer composition can be deposited on the fiber by any suitable method known to the skilled artisan.

As used herein, the term "fiber" is intended to be broadly construed and can include single or multiple filaments that can be present in a variety of ways. It should be appreciated that only a single fiber can be treated with the bioactive cationic polymer latex of the invention if so desired. Fibers that can be used in conjunction with this invention can encompass natural fibers, synthetic fibers, or any combination or mixture thereof. Natural fibers include, but are not limited to, animal fibers (for example, silk and wool); mineral fibers (for example, asbestos); and vegetable-based fibers (for example, cotton, flax, jute, and ramie). Synthetic fibers include, but are not limited to, those made from polymers such as polyamides, polyesters, acrylics, and polyolefins. Other examples of fibers include, but are not limited to, rayon and inorganic substances extruded in fibrous form such as glass, boron, boron carbide, boron nitride, carbon, graphite, aluminum silicate, fused silica, and metals such as steel. In another aspect, cellulosic or wood fibers also can be treated with the bioactive cationic polymer latex of the invention if so desired. Recycled fibers using any suitable fiber such as the above materials may also be employed. Any mixture of fibers can be treated with the bioactive cationic polymer latex of the invention if so desired.

The treated fibrous material can, in another aspect, have at least one other polymeric layer deposited on the fiber so as to form a composite fibrous structure, thus multiple polymeric layers of various types can be used if desired. For example, anionic polymer latices may be deposited on the treated fibrous material to enhance specific properties of the treated fibrous material. In another aspect, the fibrous material can be treated in a sequential fashion using, alternately, bioactive cationic polymer latices and anionic polymer latices, to form multiple layered structure. While not intending to be bound by theory, it is thought that simple coulombic interactions between cationic and anionic polymers enhance the stability of such structures, leading to treated fibrous materials that are robust. Layers of various other non-bioactive polymers can be employed similarly, for example, deposited on the cationic polymer latex which is present on the fibrous material to form a composite structure. In this fashion, unique layering architecture can be constructed with specially modified surfaces in accordance with this invention.

In a further aspect, the present invention also provides an article of manufacture comprising a substrate and a bioactive cationic polymer latex deposited or positioned thereon, as provided herein. For the purposes of this disclosure, the term "substrate" is intended to be construed and interpreted broadly to include all those formed from inorganic materials, organic materials, composites thereof, mixtures thereof, or any type of combination thereof. For example, the substrate can encompass, but is not limited to, fibers, fillers, pigments, and the like, as well as other organic and inorganic materials.

In one aspect of this invention, as disclosed herein, a fibrous substrate can be employed. The term "fibrous substrate" is also intended to be construed and interpreted broadly to include at least all the fibers, woven textiles, and non-woven textiles disclosed herein. Thus, the fibrous substrate may be present, for example, in the form of a web, a yarn, a fabric, a textile substrate, and the like. Further examples of fibrous substrates include, but are not limited to, natural fibers such as cotton and wool to synthetic fibers such as nylon, acrylics, polyesters, urethanes, and the like. Known application processes can be used to apply the bioactive cationic polymer latex, such as rod/knife coating, impregnation, back coatings, printing, as pretreatments on individual fibers, or as a finished good. Also as used herein, the term "textile substrate" can be defined according to its use in U.S. Pat. No. 5,403,640 to Krishnan et al., the disclosure of which is incorporated herein by reference in its entirety. In this aspect, for example, "textile substrate" can encompass a fiber, a web, a yarn, a thread, a sliver, a woven fabric, a knitted fabric, a non-woven fabric, an upholstery fabric, a tufted carpet, a pile carpet, and the like, including any combination thereof, formed from any of the fibers described herein.

The bioactive cationic latex composition of this invention also can be applied to a wide variety of plastic or rubber substrates. Examples of such materials include, but are not limited to, commodity molded thermoplastics such as polyolefins; engineering thermoplastics such as polysulfones, acetals, polycarbonates, and the like; thermosets such as epoxies, urethanes, and related materials; and as extruded or blown films. The polymer could be applied as a coating on the surface by rod/knife coating, spray, dipping, as a laminate coating during the extrusion process, or as a coating applied in the mold during the molding process. Rubber products could include sheets, extruded/molded articles, composites, and the like. In another aspect, the bioactive cationic latex compositions of this invention also can be deployed in solid form. In this aspect, for example, the inventive latices can be coagulated or spray-dried to provide the solid bioactive cationic latex, which can be employed in solid form as an additive in plastic products, in processes such as extrusion or blow molding, as additives for various polyethylenes, polypropylenes, and the like, and in any number of other polymer and plastic applications.

The bioactive cationic latex composition of this invention also can be applied to wood or metal substrates. In this aspect, suitable substrates would include all kinds of natural and engineered wood substrates. Suitable metal substrates would include both metals and metal alloys, such as carbon steel, stainless steel, and including solid steel bars, sheets, coils, ropes, and such, wherein the composition is applied as a coating by one of the numerous processes such as spraying dipping, brushing, roller coating, and related methods.

In this context, an article of manufacture comprising a substrate and a bioactive cationic polymer latex deposited or positioned thereon can be made in accordance with standard procedures known to one of ordinary skill in the relevant art. The article of manufacture can have, in another aspect, at least one other polymeric layer deposited thereon so as to form a composite structure, thus multiple polymeric layers of various types can be used if desired. For example, other layers of various polymers can be deposited on the bioactive cationic polymer latex which is present in the article of manufacture to form a composite structure. In this aspect, deposition of a bioactive cationic latex can be followed by the deposition of an anionic latex or other polymers to enhance specific properties of the article of manufacture. Thus, uniquely tailored articles with specially modified surfaces can be made in accordance with the present invention.

In a broader aspect, the present invention also provides a coated material comprising any material and a bioactive cationic polymer latex deposited or positioned thereon, wherein additional layers of other materials optionally can be used in combination with the bioactive cationic polymer latex of this invention. As used herein, the term "material" is intended to be used broadly to include, but not be limited to, any inorganic material, any organic material, any composite thereof, or any combination thereof. Examples of suitable materials include, but are not limited to, a fiber, a filler, a particle, a pigment, composites thereof, combinations thereof, mixtures thereof, and the like.

A multiple deposition process can also be used to make composite films that have applications in areas other than textiles and fibrous materials. In one aspect, for example, a bioactive cationic polymer latex of this invention can be used to fabricate multilayer elastomeric gloves. Cellulosic structures can also be made using the bioactive cationic polymer latex provided herein including, but not limited to, cellulosic composites and heavy duty cellulosic structures. Examples of cellulosic composites include, but are not limited to, those composites relating to filtration, shoe insoles, flooring felt, gasketing, and the like. Heavy duty cellulosic structures include, but are not limited to, dunnage bags, industrial wipes, and related structures. In a further aspect, the deposition process and bioactive cationic polymer latex of this invention also can be used in other technology arts including, but not limited to, flocculants, wet and dry strength additives for papermaking, retention aids, cement modifications, dye fixation, redispersible powders, and the like.

The present invention can afford certain advantages as compared to previous methods used to fabricate bioactive materials. In this aspect, for example, a bioactive cationic latex can be substantially deposited on a substrate such that residual bioactive latex does not remain in the processing fluid medium, providing a potential advantage from an environmental standpoint. Moreover, bioactive cationic latices can be preferentially deposited on any substrate that carries a net negative charge, and deposition can occur in a uniform manner, thereby using less latex polymer. Further to this aspect, and while not intending to be bound by theory, the bioactive cationic latex is thought to be capable of forming substantially uniform monolayers of polymer material on a negatively charged substrate, thereby allowing the use of less latex to provide the desired coverage. Because the bioactive cationic latices can be formed by existing emulsion polymerization processes, the fabrication methods advantageously allow for the preparation of high molecular weight polymers.

The bioactive cationic polymer latices disclosed herein can also obviate the need for cationic retention aids and cationic surfactants. In one aspect, for example, the bioactive cationic polymer latices can be substantially devoid of cationic surfactants. This feature can be particularly desirable because cationic surfactants generally are not retained well and can cause foaming and other adverse effects in aquatic environments. However in another aspect, this disclosure also provides for the use of bioactive agents that can exhibit cationic surfactant behavior and/or for the use of retention aids. Moreover, if desired, the polymer latices can be devoid of conventional surfactants including, for example, nonionic surfactants.

As provided herein, the latex composition of the present invention can be applied to a wide variety of substrates using various techniques that are well known to one of ordinary skill in the art. As a result, there are numerous applications for the present invention, many of which are provided in the following listing. In this aspect, while this listing is not comprehensive, specific applications include, but are not limited to: textiles such as residential and commercial carpets or tiles; liquid and air filters for HVAC or vacuum cleaners, or automotive uses; medical surgical gowns, drapes, dressings, covers, and the like; pretreatment for fibers, printed or dyed fabrics for apparel, furnishings, sheets, towels, and the like; diapers and incontinence articles; interior automotive applications such as trim, upholstery, mats, filters, and such; upholstery coatings; laminating and bonding adhesives; foams for sound absorbency; foamed articles such as pillows and mattresses; belting or other machinery parts for food handling and the like; tapes such as masking tapes, surgical tape, industrial tapes, and the like; electrical, industrial, and household cleaning wipes, cloths, and sponges; shoe products such as insoles, box toes, and such; plastic and/or rubber items such as tool handles, tool grips, toys, rubber gloves, sheets, or other articles; machinery housing such as for computers, display and diagnostic devices or instrumentation; medical devices such as catheters, balloons, tubing, syringes, diagnostic kits, and the like; packaging or product protection, as applied to perishables, computer peripherals, semiconductors, memory chips, CDs, DVDs, and the like; impact modifiers for acrylics, polycarbonates, and such; overdips or underdips for gloves such as gloves for clean rooms; breathable films; antipenetrant for fabric supported gloves; cutting boards; extruded and blown films for packaging; paper products such as vacuum bags, book covers, air filters, liquid filters, wallcoverings, wet and dry wipes, tissues, and such; felt for vinyl floor coverings; molded pulp applications; packaging such as boxes, cartons, molded articles, and related items; size press coatings for gift wraps, ink jet media, breathable coatings, and the like; wet end additives in paper, tapes, labels for use in masking, surgical applications, general purpose applications, and such; binders for use in paper; binders for use in wallboard such as gypsum wallboard and the like; adhesives for use in tapes, labels, decals, films, book bindings, pressure sensitive applications, flexible packaging and laminating adhesive (FPLA), and the like; inorganic and/or organic materials such as coating or encapsulation of fillers or pigments, construction sealers and grouts, gypsum wallboard coatings or binders, exterior or interior coatings, and the like; tile adhesives; floor coatings for use in hospitals, clean rooms, clinics, schools, and related environments; coatings for hospital and medical environments; ceiling tiles; glass fiber coatings such as glass mats, insulation, filter materials, reinforced composites, and such; coatings for air conditioning or refrigeration coils; other components for air conditioning systems, heat exchangers, ion exchangers, process water systems including cooling water treatment, solar-powered units, coated pipes, and the like; kitchen items; components of sanitary equipment; components of water systems; operator units of devices such as touch panels; materials used in bathrooms such as shower curtains, fixtures, toilet items, and even jointing or sealing compounds; medical devices such as use in coatings for stents, implants, prostheses, catheters, tubing, contact lenses, contact lens cleaners or storage solutions, protective or backing films, medical instruments, and other medical devices for providing the sustained action of bioactive agents; articles which are contacted by large numbers of people such as telephone handsets, stair rails, door handles, window catches, grab straps and grab handles in public conveyances, and the like; wound or surgical treatments; wound or surgical dressings, including any layers such as absorbent layers of wound or surgical dressings; medical or athletic tapes; surgical drapes; tapes or tabs used in adhering medical devices such as sensors, electrodes, ostomy appliances, or the like; liquid disinfectants and cleaners; personal care or hygiene products such as shampoos, lotions, creams, hair and skin care products, body wash, cosmetics, toilet items, and the like; hygiene coatings of surfaces other than floors, such as in hospitals, clinics, schools, homes, offices, and the like; hard and porous surface coatings as applicable to walls, ceilings, floors, counter tops, and the like; decorative concrete; wood such as oriented strand board (OSB) coatings; decking and construction materials for coating or impregnation; composite construction materials; furniture coatings; hygiene coatings such as used in table tops, counter tops, door knobs, door handles, fixtures, and the like; flooring applications such as in laminates, hardwood flooring, and other composite flooring materials; decorative laminates such as table tops, counter tops, furniture, and the like; other construction materials such as roofing material, wall material, facades, fencing, or for wood protection applications; marine applications such as in boat hulls, docks, buoys, drilling platforms, or ballast water tanks; metal such as cabinets, door knobs, handles, fixtures, and such; and furniture, coatings as applicable to appliances, original equipment manufacture (OEM), and the like.

In this aspect, the antimicrobial formulations of the invention can be useful as a biofouling inhibitor, in particular, in cooling circuits. To prevent damage to cooling circuits by infestation with algae or bacteria, the circuits typically have to be cleaned frequently or be appropriately oversized. In the open cooling systems usually found in power plants and in chemical plants, the addition of microbiocidal substances, such as formalin, is generally not possible. Other microbiocidal substances are frequently highly corrosive or form foams, preventing their use in systems of this type. Deposition of bacteria or algae on components of the system can thus be effectively inhibited. Therefore, the formulations and materials of this invention can be quite useful in such applications.

In another aspect, the present invention can also provide a process for sterilizing cooling-water streams or process water systems, by adding antimicrobial formulations in dispersed form to the cooling water. The dispersed form can be obtained in the preparation process itself, for example, by emulsion polymerization as detailed herein, but also by precipitation polymerization, or suspension polymerization, or subsequently by milling of the antimicrobial polymer obtained by any of these methods, for example, in a jet mill.

The antimicrobial latex polymer of this invention can be applied or used as a coating composition, which can be used for a wide variety of purposes in connection with which antimicrobial action is desired. For example, in one aspect, the antimicrobial latex polymers disclosed herein can be used in connection with a wide range of insulating materials such as wrapping materials for pipes, which are a particular risk of bacterial attack. Thus, the materials of the invention are useful when used in connection with elastomeric insulating materials. Such coating compositions can also be used in connection with industrial insulation, such as is used for insulating pipelines, examples being heating pipes, and for insulating valves and ducts. Moreover, antimicrobial latices disclosed herein can be used in conjunction with all thermal and/or acoustic insulations and related insulating materials for numerous end applications. The latices provided herein can also be used in conjunction with industrial foams and foam materials as substrates for antimicrobial coatings. Such coatings comprising the antimicrobial latices disclosed herein also can be used as coatings for air-conditioning plants, condensers, refrigerators and other refrigeration units, and also parts thereof, and also for coating compositions as paints for marine craft and for wood preservation. Coatings comprising the antimicrobial latices of this disclosure can also be employed as the coating of substrates such as metal, plastic, or ceramic, in hygiene installations, hospitals, or in the food industry, or any articles involving frequent contact of any type which may easily transmit infection pathogens, such as door handles, sanitary fittings, switches, and grips. In the case of such coatings the use of a coating composition in the form of powder coatings can be advantageous.

Applications of Antimicrobial Latices to Medical Devices

The term "medical device" as used herein refers to any material, natural or artificial, that is inserted into a mammal, or used in the process of inserting a material into a mammal. Particular medical devices suited for application of the antimicrobial latices and compositions of this invention include, but are not limited to, peripherally insertable central venous catheters, dialysis catheters, long term tunneled central venous catheters, long term non-tunneled central venous catheters, peripheral venous catheters, short-term central venous catheters, arterial catheters, pulmonary artery Swan-Ganz catheters, urinary catheters, artificial urinary sphincters, long term urinary devices, urinary dilators, urinary stents, other urinary devices, tissue bonding urinary devices, penile prostheses, vascular grafts, vascular catheter ports, vascular dilators, extravascular dilators, vascular stents, extravascular stents, wound drain tubes, hydrocephalus shunts, ventricular catheters, peritoneal catheters, pacemaker systems, small or temporary joint replacements, heart valves, cardiac assist devices and the like, bone prosthesis, joint prosthesis, dental prosthesis, and the like.

In one aspect, the medical devices that can be used in conjunction with the bioactive cationic latices of this invention include, but are not limited to, non-metallic materials such as thermoplastic or polymeric materials. Examples of such materials include rubber, plastic, polyethylene, polyurethane, silicone, GORTEX™ (polytetrafluoroethylene), DACRON™ (polyethylene tetraphthalate), polyvinyl chloride, TEFLON™ (polytetrafluoroethylene), elastomers, nylon and DACRON™ sealed with gelatin, collagen or albumin. The amount of each bioactive cationic latex used to coat the medical device varies to some extent, but is at least a sufficient amount to form an effective concentration to inhibit the growth of bacterial and fungal organisms.

The antimicrobial latices can be used alone or in combination of two or more of them. Each antimicrobial latex can comprise one or more antimicrobial components as provided herein. Any application or use disclosed herein can further encompass the use of at least one bioactive latex in conjunction with at least one other antimicrobial agent that can be dispersed throughout the surface of the medical device. The amount of each bioactive latex and each antimicrobial agent used to impregnate the medical device varies to some extent, but is at least of an effective concentration to inhibit the growth of bacterial and fungal organisms.

In one aspect, the antimicrobial agent can be selected from an antibiotic, an antiseptic, a disinfectant, or any combination thereof. In another aspect, the antimicrobial agent can be an antibiotic including, but not limited to, penicillins, cephalosporins, carbepenems, other beta-lactam antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, echinocandins, or any combination thereof.

In one aspect, at least one drug can be applied to a medical device using bioactive latices provided herein, and used in combinations with drugs that can adhere to, rather than be encapsulated by, the bioactive latices. For example, a cationic antimicrobial latex coating can be applied as a coating to a medical device that can have an ionic charge. Subsequently, drugs having a complimentary charge can be applied to, and can bind to, the charged coating applied to the surface of device when the charged coating and the drug are exposed to one another. The strength of bonding between the drug and the coating can be used to influence how readily the drug can be released from the surface of the device. In one aspect, this disclosure provides for delivering an implant or medical device having this drug delivery feature to a selected anatomical site. In this aspect, typically drugs that are useful include, but are not limited to, antimicrobials and antibiotics such as neomycin and sulfa drugs, anti-inflammatory agents such as steroidal or non-steroidal anti-inflammatory agents, or combinations thereof.

Although any methods, devices, and materials similar or equivalent to those described herein can be used in the practice or testing of the invention, the typical methods, devices and materials are herein described. All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

When Applicants disclose or claim a range of any type, for example a range of temperatures, a range of concentrations, a range of numbers of atoms, a weight percent, or the like, Applicants' intent is to disclose or claim individually each possible number that such a range could reasonably encompass, as well as any sub-ranges and combinations of sub-ranges encompassed therein. Thus, when the Applicants disclose or claim a chemical moiety having a certain number of carbon atoms, Applicants' intent is to disclose or claim individually every possible number, sub-range, and combination of sub-ranges that such a number range could encompass, consistent with the disclosure herein. For example, the disclosure that R is selected from an alkyl group having up to 12 carbon atoms, or in alternative language a $C_1$ to $C_{12}$ alkyl group, as used herein, refers to an R group that can be selected from an alkyl group having 1, 2, 3, 4, 5, 6, 7, 8, 9, 10, 11, or 12 carbon atoms, as well as any range between these two numbers for example a $C_3$ to $C_8$ alkyl group, and also including any combination of ranges between these two numbers for example a $C_3$ to $C_5$ and $C_7$ to $C_{10}$ alkyl group. Thus, Applicants retain the right to replace the terminology such as "group having up to 12 carbon atoms" with any individual number that such a range could reasonably encompass, as well as any sub-ranges and combinations of sub-ranges encompassed therein. In another example, by the disclosure that the molar ratio typically spans the range from about 0.1 to about 1.0, Applicants intend to recite that the molar ratio can be selected from about 0.1:1, about 0.2:1, about 0.3:1, about 0.4:1, about 0.5:1, about 0.6:1, about 0.7:1, about 0.8:1, about 0.9:1, or about 1.0:1, as well as any sub-ranges and combinations of sub-ranges encompassed therein. Similarly, the disclosure that a particular weight percent can be from about 80 percent to about 90 percent by weight, Applicants' intend to recite that the weight percent can be about 80 percent, about 81 percent, about 82 percent, about 83 percent, about 84 percent, about 85 percent, about 86 percent, about 87 percent, about 88 percent, about 89 percent, or about 90 percent, by weight.

Applicants reserve the right to proviso out or exclude any individual members of any such group, including any sub-ranges or combinations of sub-ranges within the group, that may be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, additives, compounds, monomers, surfactants, structures, and the like, or any groups thereof, or any individual members of a claimed group, if for any reason Applicants choose to claim less than the full measure of the disclosure, for example, to account for a reference that Applicants may be unaware of at the time of the filing of the application.

For any particular chemical compound disclosed herein, any general disclosure or structure presented also encompasses all isomers, such as conformational isomers, regioisomers, stereoisomers, and the like, that can arise from a particular set of substituents. The general structure also encompasses all enantiomers, diastereomers, and other optical isomers whether in enantiomeric or racemic forms, as well as mixtures of stereoisomers, as the context requires.

The present invention is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

In the following examples, unless otherwise specified, the reagents were obtained from commercial sources. General procedures, including general synthetic testing procedures for cationic polymer latices, are provided in U.S. Patent Application Publication Numbers 2005/0065284 and 2005/0003163, to Krishnan, each disclosure of which is incorporated herein by reference in its entirety.

Example 1

Bioactive Cationic Latex Prepared by Early Introduction of the Bioactive Agent

A one-gallon reactor can be charged with the following ingredients: about 1142 g of water; about 5.95 g of the non-ionic surfactant ABEX™ 2525 (Rhodia); about 11.90 g of methoxy polyethyleneglycolmethacrylate (MPEG 550 from Cognis); and about 31.7 g of dimethylaminoethyl methacrylate methyl chloride quaternary (AGEFLEX™ FM1Q75MC from Ciba Specialty Chemicals). The reactor contents then can be deoxygenated by subjecting the reactor to several vacuum/$N_2$ fill cycles, after which about 59.5 g of butyl acrylate and about 119 g of styrene can be added to the reactor. The reactor is again subjecting to several vacuum/$N_2$ fill cycles, after which the temperature of the reactor contents can be increased to about 165° F., at which time an initiator solution of about 23.80 g of water and about 2.38 g of WAKO V-50 (Wako Chemicals) is injected into the reaction mixture. This reaction mixture is maintained at about 165° F. for approximately 30 minutes before starting the following feeds into the reactor.

After the 30 minute "hold period," the following components can be fed into the reactor:

1) A butadiene feed consisting of about 238 g of butadiene, fed over about 5 hours;

2) A mixed monomer feed of about 102 g of butyl acrylate, about 517 g of styrene, and about 119 g of any suitable bioactive agent such as those disclosed herein. The total feed time of the entire mix can be about 5 hours. The bioactive ingredient can be introduced into the mixed monomer feed after about 1 hour of the mixed monomer feed, which involves dissolving about 119 g of the bioactive agent in about 495 g of the styrene/butyl acrylate monomer mixture that is introduced into the reactor over the final 4-hour feed period of the mixed monomer feed;

3) An aqueous monomer feed consisting of about 152 g of water, about 47.60 g of MPEG 550 (Cognis), about 47.60 g of dimethyl aminoethylmethacrylate methyl chloride quaternary (AGEFLEX™ FM1Q75MC from Ciba Specialty Chemicals), and about 74.5 g of N-methylol acrylamide. This aqueous monomer feed can be fed into the reactor over an approximately 3-hour period;

and

4) An aqueous initiator feed consisting of about 202 g of water and about 4.8 g of WAKO™ V-50, which can be fed into the reactor over about 5.5 hours;

When addition of the feeds is completed, the reaction is continued until most (greater than about 98%) of the monomers have reacted. The reactor contents are then cooled down and the vacuum stripped to remove unreacted monomers and to raise the solids concentration to about 40 percent by weight. If necessary or desired, the pH of the latex can be adjusted as required before stripping the reaction volatiles.

Example 2

Bioactive Cationic Latex Prepared by Late Introduction of the Bioactive Agent

An emulsion polymerization reaction can be conducted according to the details provided in Example 2, except that an approximately 49 g-sample of bioactive component can be introduced into the mixed monomer stream after about 4 hours of a 5 hour styrene/butyl acrylate feed. This process involves dissolving the bioactive agent in about 124 g of the styrene/butyl acrylate monomer mixture that is introduced into the reactor over the final 1-hour feed period of the mixed monomer feed.

Example 3

Evaluation of Cationic Latex Incorporating Antifungal Agents

Antifungal wallboard was identified as a target for the evaluation of a cationic latex incorporating an antifungal agent. The goal of this example was to deliver the antifungal agent is through a cationic polymer incorporated into the paper facing of the gypsum wallboard in a conventional wet end process used for paper making.

Several cationic polymers were made, with a variety of antifungal additives incorporated into the polymers during the polymerization process, at various levels. The polymers were tested both as coatings on paper as well as by addition in a wet end process. The main antifungal evaluations were conducted based on ASTM G-21 and ASTM D-3273, which showed that the best antifungal results were obtained using a combination of two antifungal additives (propiconazole ("PZ") and tebuconazole ("TZ")).

The coating study indicated that a PZ/TZ level of 0.4% on a wet basis had a significant inhibitory effect, and that the PZ/TZ could be transported through the wet end and deposit cleanly on the paper. A series of cationic polymers (without any additive incorporated into the polymers) were evaluated for antibacterial properties (both low and high levels of cationic monomer) using AATCC-100 method. The polymers showed >99% kill, whereas a control polymer that was not cationic did not show any kill.

Results and Discussions:
The antifungal additives used in this study are shown in Table-1

TABLE 1

List of additives used in polymerization

| Additive Name | Chemical description | Primary use | Solubility |
|---|---|---|---|
| Amical AF | Diiodomethyltoluyl sulfone | Antifungal | Tan solid. Limited solubility in monomer |
| Microban PZ | Propiconazole | Antifungal | Waxy solid when pure. Fairly soluble |
| Microban TZ | Tebuconazole | Antifungal | White solid. Fairly soluble |
| Microban P2 | Sodium orthophenyl phenate | Antibacterial | Solid. Water soluble |
| Triclosan | Chlorodiphenyl ether | Antibacterial | Solid. Fairly soluble in monomer |
| Microban Z01 | Zinc pyrithione | Antifungal | Solid. Insoluble in monomer |

Ideally, the materials are substantially unreactive during the polymerization conditions, so they are not degraded during polymerization. In some embodiments, low levels of additive might be observed, whether due to degradation, or difficulty in extraction from the polymer latex. In any case, retention of the additive in the latex leads to retention of antifungal properties in the finished paper.

Initial polymerization work with Amical showed that the Amical was degraded when it was incorporated in relatively high amounts. The polymerization temperature was investigated as a potential contributor to degradation, and it was kept as low as was feasible (typically <70° C.). The samples were stripped at the end of polymerization to the desired solids content.

Initial testing of the samples is shown in Table-2. This testing involved ASTM G-21, in which fungi were inoculated directly on the coated paper samples and then maintained in a humidity chamber for 28 days. The latex coating was applied on the paper using a #10 Meyer rod, and only a single coat was applied. However, it was determined that this was not an adequate coating thickness, considering that the paper may not have been fully covered, and this is reflected in the fungal growth data shown in FIG. 1.

The latex samples with the PZ/TZ combination (MB-38, MB-39) exhibited potent fungal inhibition characteristics.

Additive levels recovered from the latex samples were determined and compared with the amounts of additives originally added. This data is summarized in Table-2.

TABLE 2

Analytical data on the additive levels in latex

| 40% solid latex emulsions | Actives loaded into cationic latex particles during polymerization (ppm based on weight of wet latex emulsion) | Analytical based on wet latex emulsion (ppm) |
|---|---|---|
| MB37 (AF) | 10000 | 95 |
| MB26 (AF) | 4000 | 38 |
| MB19 (AF) | 2000 | 19 |
| MB28 (P2/TZ) | 1000/1000 | 14/790 |

TABLE 2-continued

Analytical data on the additive levels in latex

| 40% solid latex emulsions | Actives loaded into cationic latex particles during polymerization (ppm based on weight of wet latex emulsion) | Analytical based on wet latex emulsion (ppm) |
| --- | --- | --- |
| MB29 (P2/TZ) | 2000/2000 | 310/330 |
| MB38 (PZ/TZ) | 1000/1000 | 620/620 |
| MB39 (PZ/TZ) | 2000/2000 | 1700/1400 |
| MB47 (ZO1) | 2000 | 0 |
| MB48 (ZO1) | 4000 | 190 |
| MB30 (B) | 2000 | 1600 |

In this example, Amical tended to be poorly incorporated into the latex even when significant amounts were added during polymerization. Significant amounts of the PZ/TZ combination, as well as triclosan, were recovered.

Figure 2:
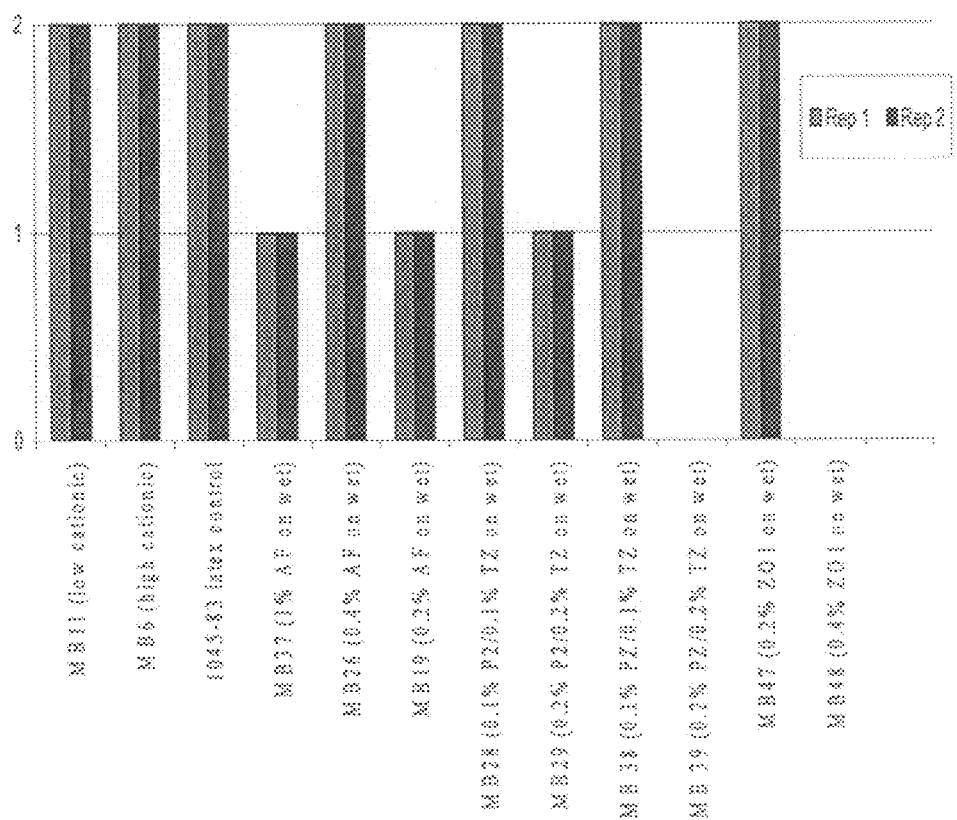
FIG. 2 is a graph showing the results of a 30-III fungal test, based on making a 1"X1" chip of the dried latex, inoculating the fungal species directly on to the sample, and then observing its growth after 7 days.

The results observed in the G-21 study were also duplicated in a shorter (7 day incubation) fungal study (referred to herein as 30-III). The results are shown in FIG. 2. Microban Z01, zinc pyrithione at 0.4% (wet basis), and PZ/TZ all performed well.

The 30-III fungal test was based on making a 1"X1" chip of the dried latex and inoculating the fungal species directly on to the sample and then observing its growth after 7 days. This is not as rigorous a test as the G-21 test, but gave a quick indication of the efficacy of the additives. In this test, the Amical samples showed some fungal inhibition.

In this test, the cationic polymers by themselves, without any additive, did not exhibit significant fungal resistance qualities. Variation of the cationic charge did not seem to affect the antifungal performance. This is in contrast to a different antifungal test where a polymer film was inoculated with a fungal species and left in a humidity chamber for 6 months without any fungal growth. One reason for this result could be that the films tested were much thicker films (about 4 mils or 100 microns) than those tested here.

Figure 3:
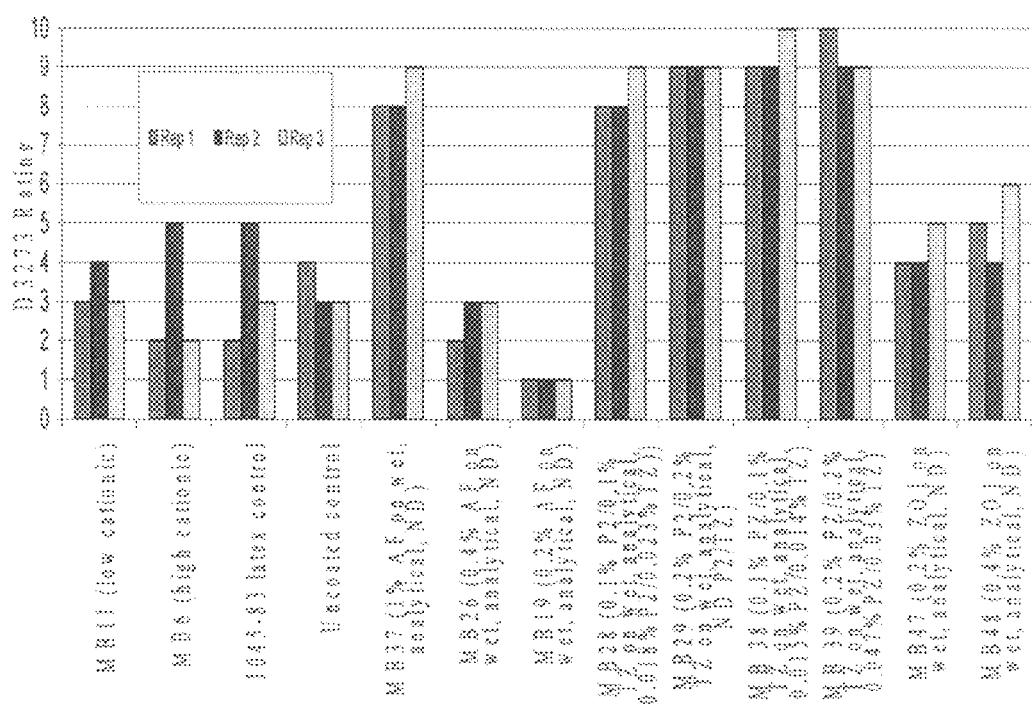
FIG. 3 is a graph showing the results of a second round of testing of coated paper samples, tested according to ASTM D-3273 over a period of 28 days. In this study, the fungal species were not directly inoculated on the surface, but rather, were maintained in the humidity chamber as spores that would then land on the surface of the coated paper.

A second round of testing was performed using an increased coating thickness to ensure full coverage of the paper surface. The second round of testing of the coated paper samples were tested according to ASTM D-3273. In this study, the duration remained the same (28 days), but the fungal species were not directly inoculated on the surface. Rather, they were maintained in the humidity chamber as spores that would then land on the surface of the coated paper as in a real world example. The results of this study are outlined in FIG. 3.

In this study, Amical and PZ/TZ were effective, but Z01 did not perform well. The cationic polymers without any additive also did not seem to show antifungal properties, and appeared to be similar to the uncoated paper samples. The analytical data shown in FIG. 3 was based on measurements of the coated sample before the start of the fungal study. The recovery of the additive from the paper is not quantitative.

The next phase of the study was to demonstrate that the same performance could be obtained through the wet end process same as in coated paper. The deposition of latex on to paper involved depositing a fixed amount of latex (10% based on fiber) on to softwood fibers and sending these for antifungal evaluations. The amount of additive in the latex was around 7.5% (in one sample, 2.5% PZ and 5% TZ by weight). This data is summarized in FIG. 4. In this study, paper samples were made using the cationic latex with (MB-87) and without the PZ/TZ additive (MB-86). As mentioned earlier, the amount of PZ/TZ additive in the latex was ~7.5% (dry basis). This would give about 6680 ppm of PZ/TZ in the finished paper and 10% polymer or latex on a fiber basis weight.

Figure 4:
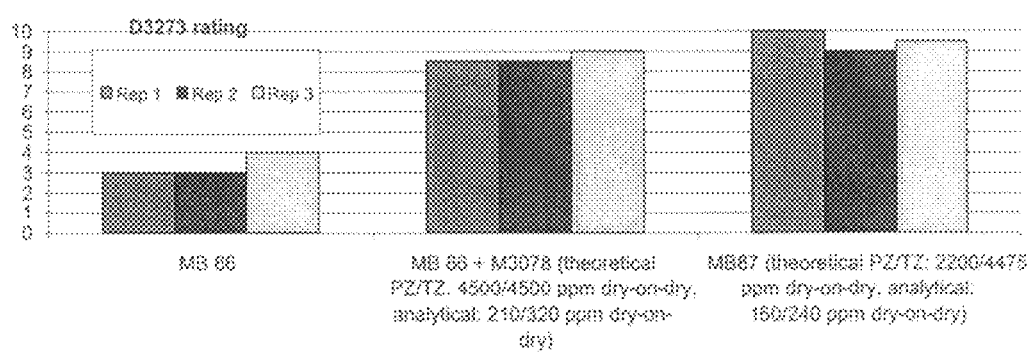
FIG. 4 is a graph showing the evaluation of the antimicrobial properties of paper in which an antimicrobial latex was incorporated into the paper in a wet end process, as compared to coated paper, using ASTM D-3273.

A dispersion of PZ/TZ (M-3078) was also provided, with an activity of 28%. This was used as a post add with the cationic latex MB-86 to give essentially the same amount of PZ/TZ. Hence, the post added sample with the dispersion had a PZ/TZ concentration of about 10%, much more than that of the polymerized latex sample, and would result in a PZ/TZ concentration of around 9000 ppm in the finished paper. The antifungal results of the plain latex (MB-86), MB-86 with post added PZ/TZ, and the polymerized PZ/TZ sample MB-87 is shown in FIG. 4.

Just as in the coated sample study, the paper with just the cationic latex did not pass the fungal D-3273 test. Both the post added and the polymerized PZ/TZ samples passed the test. It should be noted that the polymerized additive sample (MB-87) had 3000 ppm less of the PZ/TZ, but still seemed to perform as well as or slightly better than the post added sample. No fungal growth was observed.

In the specification, typical embodiments have been disclosed and, although specific terms are employed, they are used in a generic and descriptive sense and not for purposes of limitation. It should be clearly understood that resort can be had to various other embodiments, aspects, modifications, and equivalents to those disclosed in the claims, which, after reading the description herein, may suggest themselves to one of ordinary skill in the art without departing from the spirit of the present disclosure or the scope of these claims. The following claims are provided to ensure that the present application meets all statutory requirements as a priority application in all jurisdictions and shall not be construed as setting forth the full scope of the latex composition, methods for use of same, and articles incorporating or containing same that are disclosed herein.

I claim:

1. A bioactive cationic polymer latex comprising:
   a) a latex polymer comprising the polymerization product of: i) at least one ethylenically unsaturated first monomer; and ii) at least one ethylenically unsaturated second monomer that is cationic or a precursor to a cation;
   b) at least one bioactive component at least partially encapsulated within the latex polymer during emulsion polymerization; and
   c) optionally, at least one sterically bulky component incorporated into the latex polymer.

2. The bioactive cationic polymer latex according to claim 1, wherein the at least one ethylenically unsaturated first monomer is selected independently from a vinyl aromatic monomer, a halogenated or a non-halogenated olefin monomer, an aliphatic conjugated diene monomer, a non-aromatic unsaturated mono- or dicarboxylic ester monomer, a monomer based on the half ester of an unsaturated dicarboxylic acid monomer, an unsaturated mono- or dicarboxylic acid monomer, a nitrile-containing monomer, a cyclic or an acyclic amine-containing monomer, a branched or an unbranched alkyl vinyl ester monomer, a halogenated or non-halogenated alkyl acrylate monomer, a halogenated or non-halogenated aryl acrylate monomer, a carboxylic acid vinyl ester, an acetic acid alkenyl ester, a carboxylic acid alkenyl ester, a vinyl halide, a vinylidene halide, or any combination thereof, any of which having up to 20 carbon atoms.

3. The bioactive cationic polymer latex according to claim 1, wherein the at least one ethylenically unsaturated first monomer is selected independently from styrene, para-methyl styrene, chloromethyl styrene, vinyl toluene, ethylene, butadiene, methyl (meth)acrylate, ethyl (meth)acrylate, propyl (meth)acrylate, butyl (meth)acrylate, pentyl (meth)acrylate, glycidyl (meth)acrylate, isodecyl (meth)acrylate, lauryl (meth)acrylate, monomethyl maleate, itaconic acid, (meth) acrylonitrile, (meth)acrylamide, N-methylol (meth)acrylamide, N-(isobutoxymethyl)(meth)acrylamide, vinyl neodecanoate, vinyl versatates, vinyl acetate, a $C_3$-$C_8$ alkyl vinylether, a $C_3$-$C_8$ alkoxy vinylether, vinyl chloride, vinylidene chloride, vinyl fluoride, vinylidene fluoride, trifluoroethylene, tetrafluoroethylene, chlorotrifluoroethylene, hexafluoropropylene, chlorotrifluoroethylene, perfluorobutyl ethylene, a perfluorinated $C_3$-$C_8$ alpha-olefin, a fluorinated $C_3$-$C_8$ alkyl vinylether, a perfluorinated $C_3$-$C_8$ alkyl vinylether, a perfluorinated $C_3$-$C_8$ alkoxy vinyl ether, or any combination thereof.

4. The bioactive cationic polymer latex according to claim 1, wherein the at least one ethylenically unsaturated second monomer is selected independently from an amine monomer, an amide monomer, a quaternary amine monomer, a phosphonium monomer, a sulfonium monomer, or any combination thereof, any of which having up to 20 carbon atoms.

5. The bioactive cationic polymer latex according to claim 1, wherein the at least one ethylenically unsaturated second monomer is selected independently from dimethylaminoethyl acrylate; diethylaminoethyl acrylate; dimethyl aminoethyl methacrylate; diethylaminoethyl methacrylate; tertiary butylaminoethyl methacrylate; N,N-dimethyl acrylamide; N,N-dimethylaminopropyl acrylamide; acryloyl morpholine; N-isopropyl acrylamide; N,N-diethyl acrylamide; dimethyl aminoethyl vinyl ether; 2-methyl-1-vinyl imidazole; N,N-dimethyl-aminopropyl methacrylamide; vinyl pyridine; vinyl benzyl amine; dimethylaminoethyl acrylate, methyl chloride quarternary; dimethylaminoethyl methacrylate, methyl chloride quarternary; diallyldimethylammonium chloride; N,N-dimethylaminopropyl acrylamide, methyl chloride quaternary; trimethyl-(vinyloxyethyl) ammonium chloride; 1-vinyl-2,3-dimethylimidazolinium chloride; vinyl benzyl amine hydrochloride; vinyl pyridinium hydrochloride; or any combination thereof.

6. The bioactive cationic polymer latex according to claim 1, wherein the at least one sterically bulky component is selected independently from at least one sterically bulky ethylenically unsaturated third monomer, at least one sterically bulky polymer, or any combination thereof.

7. The bioactive cationic polymer latex according to claim 1, wherein the at least one sterically bulky component is at least one a sterically bulky ethylenically unsaturated third monomer selected independently from:
   a) $CH_2=C(R^{1A})COO(CH_2CHR^{2A}O)_m R^{3A}$, wherein $R^{1A}$, $R^{2A}$, and $R^{3A}$ are selected independently from H or an alkyl group having from 1 to 6 carbon atoms, inclusive, and m is an integer from 1 to 30, inclusive;
   b) $CH_2=C(R^{1B})COO(CH_2CH_2O)_n(CH_2CHR^{2B}O)_p R^{3B}$, wherein $R^{1B}$, $R^{2B}$, and $R^{3B}$ are selected independently from H or an alkyl group having from 1 to 6 carbon atoms, inclusive, and n and p are integers selected independently from 1 to 15, inclusive;
   c) $CH_2=C(R^{1C})COO(CH_2CHR^{2C}O)_q(CH_2CH_2O)_r R^{3C}$, wherein $R^{1C}$, $R^{2C}$, and $R^{3C}$ are selected independently from H or an alkyl group having from 1 to 6 carbon atoms, inclusive, and q and r are integers selected independently from 1 to 15, inclusive; or
   d) any combination thereof.

8. The bioactive cationic polymer latex according to claim 1, wherein the at least one sterically bulky component is at least one sterically bulky ethylenically unsaturated third monomer selected independently from:
   a) $CH_2=C(R^{1A})COO(CH_2CHR^{2A}O)_m R^{3A}$, wherein $R^{1A}$, $R^{2A}$, and $R^{3A}$ are selected independently from H or methyl, and m is an integer from 1 to 10, inclusive;
   b) $CH_2=C(R^{1B})COO(CH_2CH_2O)_n(CH_2CHR^{2B}O)_p R^{3B}$, wherein $R^{1B}$, $R^{2B}$, and $R^{3B}$ are selected independently from H or methyl, and n and p are integers selected independently from 1 to 10, inclusive;
   c) $CH_2=C(R^{1C})COO(CH_2CHR^{2C}O)_q(CH_2CH_2O)_r R^{3C}$, wherein $R^{1C}$, $R^{2C}$, and $R^{3C}$ are selected independently from H or methyl, and q and r are integers selected independently from 1 to 10, inclusive; or
   d) any combination thereof.

9. The bioactive cationic polymer latex according to claim 1, wherein the at least one sterically bulky component is selected independently from: an alkoxylated monoester of a dicarboxylic acid; an alkoxylated diester of a dicarboxylic acid; a polyoxyethylene alkylphenyl ether; a polymerizable surfactant; or any combination thereof.

10. The bioactive cationic polymer latex according to claim 1, wherein the at least one sterically bulky component is at least one sterically bulky polymer selected independently from polyvinyl alcohols, polyvinyl pyrollidone, hydroxyethyl cellulose, or any combination thereof.

11. The bioactive cationic polymer latex according to claim 1, wherein the at least one bioactive component is selected independently from undecylenic acid; undecylenic alcohol; the reaction product of undecylenic acid with hydroxylethyl (meth)acrylate or polyethylene glycol (meth)acrylate; the reaction product of undecylenic alcohol with (meth)acrylic acid, maleic anhydride, or itaconic acid; chitosan or modified chitosans; or any combination thereof.

12. The bioactive cationic polymer latex according to claim 1, wherein the at least one bioactive component is selected independently from copper, copper salts, silver, silver salts, zinc, zinc salts, silver oxide, zinc oxide, chlorhexidine, chlorhexidine gluconate, glutaral, halazone, hexachlorophene, nitrofurazone, nitromersol, povidone-iodine, thimerosol, $C_1$- to $C_5$-parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, pyrithione salts, sodium pyrithione, zinc pyrithione, (dodecyl) (diethylenediamine) glycine, (dodecyl) (aminopropyl) glycine, phenol, m-cresol, o-cresol, p-cresol, o-phenyl-phenol, resorcinol, vinyl phenol, polymeric guanidines, polymyxins, bacitracin, circulin, octapeptins, lysozmye, lysostaphin, cellulytic enzymes, vancomycin, ristocetin, actinoidins, avoparcins, tyrocidin A, gramicidin S, polyoxin D, tunicamycin, neomycin, streptomycin, 5-chloro-2-(2,4-dichlorophenoxyl)phenol, or any combination thereof.

13. The bioactive cationic polymer latex according to claim 1, wherein the at least one bioactive component is selected independently from propiconazole, tebuconazole, azaconazole, biternatol, bromuconazole, cyproconazole, diniconazole, fenbuconazole, flusilazole, flutnafol, imazalil, imibenconazole, metconazole, paclobutrazol, perfuazoate, penconazole, simeconazole, triadimefon, triadimenol, uniconazole, mancozeb, maneb, metiram, zineb, fludioxonil, fluquinconazole, difenoconazole, 4,5-dimethyl-N-(2-propenyl)-2-(trimethylsilyl)-3-thiophenecarboxamide (sylthiopham), hexaconazole, etaconazole, triticonazole, flutriafol, epoxiconazole, bromuconazote, tetraconazole, myclobutanil, bitertanol, pyremethanil, cyprodinil, tridemorph, fenpropimorph, kresoxim-methyl, azoxystrobin, fenpiclonil, benalaxyl, furalaxyl, metalaxyl, R-metalaxyl, orfurace, oxadixyl, carboxin, prochloraz, triflumizole, pyrifenox, acibenzolar-S-methyl, chlorothalonil, cymoxanil, dimethomorph, famoxadone, quinoxyfen, fenpropidine, spiroxamine, triazoxide, hymexazole, pencycuron, fenamidone, guazatine, benomyl, captan, carbendazim, capropamid, ethirimol, flutolanil, fosetyl-aluminum, fuberidazole, hymexanol, kasugamycin, iminoctadine-triacetate, ipconazole, iprodione, mepronil, metalaxyl-M (mefenoxam), nuarimol, oxine-copper, oxolinic acid, perfurazoate, propamocarb hydrochloride, pyroquilon, quintozene, silthiopham, tecnazene, thiabendazole, thifluzamide, thiophenate-methyl, thiram, tolclofos-methyl, triflumizole, or any combination thereof.

14. The bioactive cationic polymer latex according to claim 1, comprising from about 20 percent to about 99.5 percent by weight of the ethylenically unsaturated first monomer, based on the total monomer weight.

15. The bioactive cationic polymer latex according to claim 1, comprising from about 0.01 percent to about 75 percent by weight of the ethylenically unsaturated second monomer, based on the total monomer weight.

16. The bioactive cationic polymer latex according to claim 1, comprising from about 0.01 percent to about 40 percent by weight bioactive additive, based on the total monomer weight.

17. The bioactive cationic polymer latex according to claim 1, comprising from 0 percent to about 25 percent by weight sterically bulky component, based on the total monomer weight.

18. The bioactive cationic polymer latex according to claim 1, further comprising a nonionic surfactant.

19. The bioactive cationic polymer latex according to claim 1, wherein the latex polymer is substantially devoid of cationic and anionic surfactants.

20. A coating comprising the bioactive cationic polymer latex according to claim 1.

21. An article comprising the bioactive cationic polymer latex according to claim 1.

22. The bioactive cationic polymer latex according to claim 1, wherein the at least one bioactive component is a fungicide.

23. The bioactive cationic polymer latex according to claim 1, wherein the at least one ethylenically unsaturated second monomer is dimethylaminoethyl methacrylate.

24. The bioactive cationic polymer latex according to claim 1, wherein the at least one ethylenically unsaturated second monomer is dimethylaminoethyl methacrylate, methyl chloride quarternary.

25. A personal care or hygiene product comprising
a) a latex polymer comprising the polymerization product of: i) at least one ethylenically unsaturated first monomer; and ii) at least one ethylenically unsaturated second monomer that is cationic or a precursor to a cation;
b) at least one bioactive component at least partially encapsulated within the latex polymer during emulsion polymerization; and
c) optionally, at least one sterically bulky component incorporated into the latex polymer.

26. The personal care product according to claim 25, wherein the personal care product is a shampoo, lotion, cream, body wash, or cosmetic.

27. The personal care product according to claim 25, wherein the at least one ethylenically unsaturated second monomer is dimethylaminoethyl methacrylate.

* * * * *